(12) United States Patent
Paris

(10) Patent No.: US 10,521,765 B2
(45) Date of Patent: Dec. 31, 2019

(54) MATERIAL TRACKING SYSTEM

(71) Applicant: Marion E. Paris, Lincolnton, NC (US)

(72) Inventor: Marion E. Paris, Lincolnton, NC (US)

(73) Assignee: PCT LTD, Little River, SC (US)

( * ) Notice: Subject to any disclaimer, the term of this patent is extended or adjusted under 35 U.S.C. 154(b) by 0 days.

(21) Appl. No.: 15/619,062

(22) Filed: Jun. 9, 2017

(65) Prior Publication Data

US 2017/0286904 A1 Oct. 5, 2017

Related U.S. Application Data

(63) Continuation-in-part of application No. 14/305,865, filed on Jun. 16, 2014, now Pat. No. 9,679,170.

(60) Provisional application No. 62/412,549, filed on Oct. 25, 2016, provisional application No. 61/835,892, filed on Jun. 17, 2013.

(51) Int. Cl.
| | |
|---|---|
| *H04Q 5/22* | (2006.01) |
| *G06Q 10/08* | (2012.01) |
| *G08B 21/18* | (2006.01) |
| *A61L 2/24* | (2006.01) |
| *A61L 2/18* | (2006.01) |

(52) U.S. Cl.
CPC .............. *G06Q 10/087* (2013.01); *A61L 2/18* (2013.01); *A61L 2/24* (2013.01); *G08B 21/182* (2013.01)

(58) Field of Classification Search
None
See application file for complete search history.

(56) References Cited

U.S. PATENT DOCUMENTS

| 6,652,495 B1 | 11/2003 | Walker |
| 9,679,170 B2 | 6/2017 | Paris, Jr. et al. |
| 2005/0265889 A1 | 12/2005 | Wu et al. |
| (Continued) | | |

FOREIGN PATENT DOCUMENTS

| EP | 3316189 A1 | 5/2018 |
| WO | 2014204857 A1 | 12/2014 |

OTHER PUBLICATIONS

Written Opinion and Search Report received in corresponding PCT Appl. PCT/US2014/042545, dated Oct. 17, 2014, 11-pgs.
(Continued)

*Primary Examiner* — Adolf Dsouza
(74) *Attorney, Agent, or Firm* — Blank Rome LLP

(57) ABSTRACT

A system monitors the distribution of a disinfectant having an expiration. The system has distribution containers and use containers, each having a volume for dispensing the disinfectant. A reader of the system can read identifiers associated with the containers, and a database of the system can associate the volumes and the expiration of the disinfectant contained in each of the containers. During monitoring, processing equipment of the system tracks each of the volumes of the disinfectant, the expiration of the disinfectant, and the identifiers of the containers. For example, the processing equipment can log the dispensing of the disinfectant from the distribution container to the use containers and can log any amount of the dispensed disinfectant in the use containers that was noted used. Additionally, the processing equipment can determine that the distribution container or any of the user containers have disinfectant past the expiration.

38 Claims, 21 Drawing Sheets

(56) References Cited

U.S. PATENT DOCUMENTS

| | | | |
|---|---|---|---|
| 2008/0190953 A1* | 8/2008 | Mallett | A61L 11/00 221/13 |
| 2011/0084835 A1* | 4/2011 | Whitehouse | A61B 1/00059 340/540 |
| 2013/0204227 A1 | 8/2013 | Bochenko | |
| 2014/0379874 A1 | 12/2014 | Starr et al. | |

OTHER PUBLICATIONS

Extended European Search Report dated Mar. 21, 2018 in European Counterpart application No. 17198413.1.

* cited by examiner

660

DISPENSER                           | CLEAR ALL |
☐ REFILL
☐ HANDHELD LOGIN
☐ WASTE AMOUNT           662       | UPDATE ALL |
☐ DISPENSE
☐ DRUM SCANNED
☐ WASTE AMOUNT                      | EXPORT |

664

| SENSOR ID | SKU DESCRIPTION | EVENT | EVENT DATE |
|---|---|---|---|
| 69177 | 32OZ BOTTLE | REFILL | 03/31/13 4:26PM |
| 34133 | 25 GAL DRUM | DRUM SCANNED | 03/31/13 4:26PM |
| 25798 | 16 OZ BOTTLE | DISPENSE | 03/31/13 4:26PM |
| 64332 | HAND DISPENSER | WASTE AMOUNT | 03/31/13 4:26PM |

*FIG. 6G*

700B Disinfectant Bottle Based on tag

Current Expiration Date: reads date currently coded on bottle

Hello! This is a DISINFECTANT bottle.
Do you want to refill it?

YES   NO (Yes + Continue = Next Page)   (No + Continue = Exit to Start Screen)

The continue button also assigns the new expiration date the bottle in the background, before user moves it away from the reader.

FIG. 7B

700C Disinfectant Bottle based on tag

Ok, perfect...

If there is anything left in this bottle, pour it out.
Then, fill it completely with Anolyte.

When you finish, press this button:

FINISH   Finished Button = Next Page
Sends tag info to cloud for App

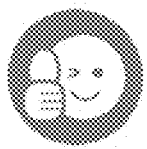

You're Done!

You just made a non-toxic hospital strength disinfectant.
Happy Cleaning!

New Expiration Date: New expiration date populates here

RETURN TO HOMEPAGE return to home screen = logout or present another bottle

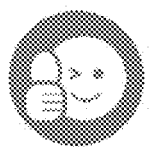

It's that easy!

You just made an ecofriendly sanitizer.

New Expiration Date: New expiration date populates here

RETURN TO HOMEPAGE return to home screen = logout or present another bottle

Electrostatic Based on tag

Current Expiration Date: reads date currently coded on bottle

Hello! This is an ELECTROSTATIC container.
Do you want to refill it?

YES   NO (Yes + Continue = Next Page)   (No + Continue = Exit to Start Screen)

Electrostatic Based on tag

Just like a disinfectant bottle, empty all the contents and fill the container completely with Anolyte.

When you finish, press this button:

FINISH   Finished Button = Next Page
Sends tag info to cloud for App

FIG. 7L

FIG. 7M
© 2016 PARADIGM CONVERGENCE TECHNOLOGIES
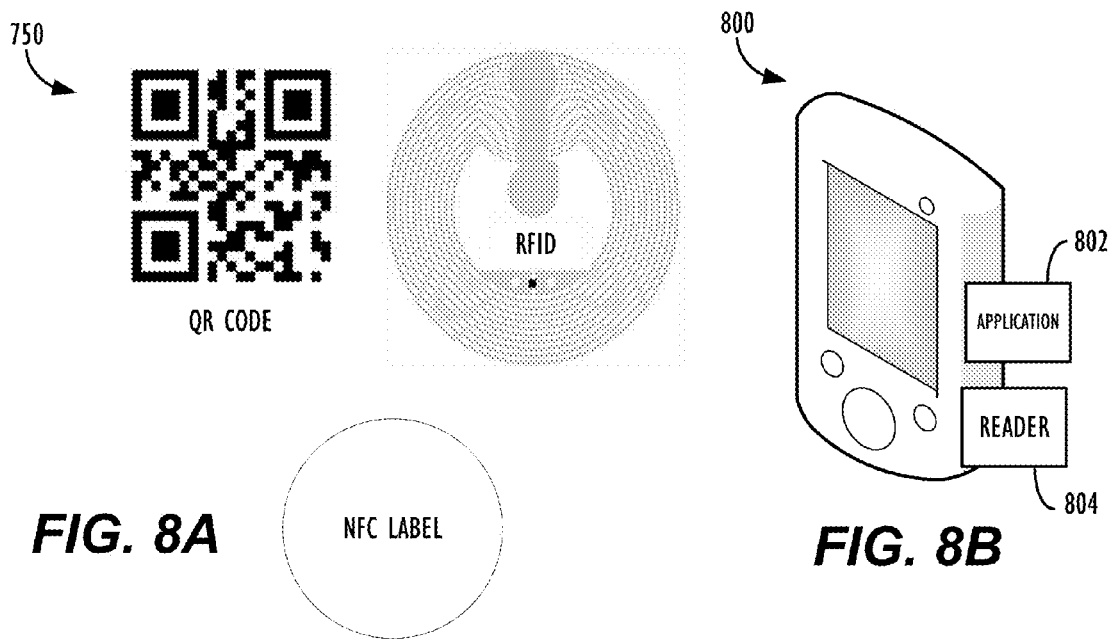
FIG. 8A
FIG. 8B 1100 

Room Report

Room #: 110

Personnel:

Date/time room last cleaned: 07/99/99

Time in room
 Time entered room: 10:02am
 Time left room: 10:46am

Tasks completed in room:
 Bed change: Yes
 Electrostatic Spray terminal clean disinfection: No
 Bathrooms cleaned, disinfected and stocked: Yes
 High touch areas and counters disinfected: Yes
 Proper handling and disposal: Yes Pathogen Alert:
 Name of pathogen: C. diff
 Extra precautions and procedures:
 Extra PPE and Barrier Protection, complete cleaning of all hard surfaces and a 10 minute dwell time full disinfection.

Tasks completed in room:
 Bed change: Yes
 Electrostatic Spray terminal clean disinfection: No
 Bathrooms cleaned, disinfected and stocked: Yes
 High touch areas and counters disinfected: Yes
 Proper handling and disposal: Yes Pathogen Alert:
 Name of pathogen: C. diff
 Extra precautions and procedures:
 Extra PPE and Barrier Protection, complete cleaning of all hard surfaces and a 10 minute dwell time full disinfection.

DISINFECTANT:
 Dispensed Date: 09/99/99
 Expiration Date: 10/99/99

Hands washed: Yes

Comments:

*FIG. 11*

MATERIAL TRACKING SYSTEM

CROSS-REFERENCE TO RELATED APPLICATION

This application claims the benefit of U.S. Prov. Appl. 62/412,549, filed 25 Oct. 2016 and is also a continuation-in-part application of U.S. application Ser. No. 14/305,865, filed 16 Jun. 2014, which claims the benefit of U.S. Prov. Appl. 61/835,892, filed 17 Jun. 2013.

FIELD OF THE DISCLOSURE

This disclosure relates generally to a method and apparatus for tracking disinfectant materials that have a limited effective life span, such as hypochlorous acid, used in sites such as healthcare facilities and schools.

BACKGROUND

Hypochlorous acid (HOCl) is a weak acid that has many characteristics that can be utilized for beneficial purposes. One such beneficial characteristic is that hypochlorous acid is a highly effective disinfecting agent that kills many types of dangerous infectious bacteria and viruses. Although the human body produces hypochlorous acid to fight infections, hypochlorous acid can also be artificially synthesized.

While it is highly effective at destroying bacteria and viruses that are harmful or deadly to humans such as *E. Coli*, MRSA (Staph), *Salmonella*, Tuberculosis, HIV, and SARs, hypochlorous acid is also relatively harmless to humans at its typical effective disinfectant concentrations and is therefore safe to use in facilities such as hospitals, nursing homes, and schools. Current disinfectants used by these types of facilities are not as effective as hypochlorous acid, and it is not uncommon for patients and visitors to contract serious illnesses from the bacteria and viruses at these facilities. The inability to effectively combat the infectious organisms that are present in these facilities increases healthcare costs and creates physical harms to patients that are easily preventable by using more effective disinfectants such as hypochlorous acid.

Although hypochlorous acid is highly effective as a disinfectant, its effectiveness has a limited duration. Hypochlorous acid owes much of its effectiveness as a disinfectant to its oxygen atom. The oxygen atom is responsible for oxidizing and destroying the cell walls of microorganisms. However, over time, hypochlorous acid decomposes to chloric acid, hydrochloric acid, and oxygen, none of which exhibit the same desirable disinfectant properties as hypochlorous acid. The typical effective period for hypochlorous acid as a disinfectant may be around 30 days from the time it is produced. Therefore, time-tracking hypochlorous acid used in a hospital or any similar setting where this highly effective disinfectant is utilized becomes crucial in maintaining and ensuring sterile environments.

Additionally, to be used in hospitals or settings that require a sterile environment, disinfectant processes must typically be substantiated by governmental agencies such as the Environmental Protection Agency (EPA) or Food and Drug Administration (FDA). Due to the time-critical factor of the effectiveness of hypochlorous acid, these agencies would only be likely to substantiate processes that utilize hypochlorous acid as a disinfecting agent if the process included an accurate mechanism for validating that any material used is within its effective period. This becomes a complicated process as these materials may be delivered to a facility in a container having a relatively large volume and may then be dispensed into many containers having smaller volumes for use. Accordingly, validating the effectiveness of any material used involves tracking the contents of a large number of containers. There is therefore a need in the art to overcome these difficulties in order to track highly effective disinfectants having a limited lifespan, such as hypochlorous acid.

SUMMARY OF THE DISCLOSURE

According to the present disclosure, a system is used for monitoring treatment of locations of a facility with a disinfectant that is expirable, meaning that the disinfectant has an expiration, a limited duration of effectiveness, an effective period, a designated shelf life, or the like.

The system comprises a plurality of first identifiers, communication equipment, at least one database, and processing equipment. The first identifiers are electronically readable and are associated with a plurality of containers each having a volume that is fillable repeatedly with the disinfectant for use in the treatment. For example, the first identifiers can be a Radio Frequency Identification tag, a bar code, a quick response (QR) code, a magnetic strip, a near field communication element, an optical element, and an electromagnetic element. The containers can be a spray bottle, an electrostatic sprayer, a hand-sanitizer dispenser, a disinfectant container, and a sanitation container.

The communication equipment obtains electronic input at least of each first identifier associated with the containers before use in the treatment. The at least one database associates first information of each first identifier for each container with each volume and each expiration of the disinfectant filled in each container The processing equipment is operatively coupled to the at least one database and the communication equipment. The processing equipment tracks the first information using the electronic input and alerts an issue with the disinfectant in a given one of the containers before the use in the treatment based on the tracking.

The communication equipment can be a reader for electronically reading the first identifiers before the use in the treatment. For example, the reader can be a Radio Frequency Identification (RFID) reader, an optical scanner, a barcode reader, a Quick Response (QR) code reader, a magnetic strip reader, a near field communication device, an optical device, and an electromagnetic device. The communication equipment can also be a user interface associated with the processing equipment.

The processing equipment can be a server, a computer, a tablet, a laptop computer, a kiosk, a cellular phone, and a smart phone and can be shared with some of the communication equipment.

To track the first information, the processing equipment is configured to log the filling of each volume of the disinfectant in each container. For example, the processing equipment can be configured to measure the disinfectant dispensed in the filling.

To alert the issue with the disinfectant, the processing equipment can configured to execute one or more rules. For example, the processing equipment can generate an alert when the given container indicates containing the disinfectant past the expiration, can automatically dispose of the disinfectant from the given container indicated to contain the disinfectant past the expiration, or can instruct manual disposal of the disinfectant from the given container indicated to contain the disinfectant past the expiration.

To track, the processing equipment can be configured to determine that the given container contains the disinfectant past the expiration. In this way, the processing equipment can alert the expiration based on the determination. To track, the processing equipment can be configured to determine that the volume of the disinfectant in the given container has been depleted. In this way, the processing equipment can alert the depletion based on the determination.

One of the first identifiers can identify a distribution container being filled with the disinfectant at a source and transported to the facility for dispensing. Another of the first identifiers can identify a use container being filled with the disinfectant from the distribution container for use at the facility.

The processing equipment can be a local processing unit at the facility. The processing equipment can further include a remote processing unit operatively coupled to the local processing unit via a network connection.

In a further configuration, second identifiers are electronically readable and are associated with the locations for the treatment with the disinfectant. Accordingly, the at least one database associate the locations with the first information, and the communication equipment obtains the locations as part of the electronic input. The processing equipment further tracks the locations in conjunction with the first information.

To alert the issue in this configuration, the processing equipment is configured to alert the expiration of the disinfectant associated with one of the first identifiers being used for the treatment of the location associated with one of the second identifiers. Again, the communication equipment can be at least one reader electronically reading the second identifiers. To track the locations in this configuration, the processing equipment is configured to associate a type of the treatment performed at the location, a user performing the treatment at the location, and a time of the treatment at the location.

At least one device in this configuration can obtain information from the first and second identifier for the containers and locations. For example, the at least one device can include a unit having a first reader electronically reading the first identifiers of the containers and being operable to fill the containers. The at least one device can also include a user interface having a second reader electronically reading the second identifiers of the locations and being operable to associate the second identifiers with the first identifiers of the given containers used. To do this association, the second reader of the user interface can electronically read the first identifiers to associate the first identifiers with the second identifiers.

According to one arrangement, the system comprises generation equipment producing the disinfectant. For example, a unit can have the generation equipment incorporated therein with at least one component of one or more of the communication equipment, the at least one database, and the processing equipment. The disinfectant used with the system can include more than one disinfectant type, and the generation equipment of the system can produce at least one of the more than one disinfectant type.

In general, the disinfectant types that can be produced by the generation equipment can include a first concentration of hypochlorous acid (HOCl) solution produced through an electrolytic process, a second concentration of hypochlorous acid (HOCl) solution produced through the electrolytic process and being less than the first concentration, a catholyte solution produced as a byproduct of the electrolytic process, a sodium hydroxide solution, a solution of negatively charged electrolyzed water, and an electrostatic solution. Given these various disinfection types, the at least one database of the system can associate each disinfectant type with the stored and tracked information related to the types of user containers, types of treatments, the treatment locations, etc. The processing equipment can then track each disinfectant type in conjunction with this stored and tracked information. In this way, for example, the processing equipment can alert that the disinfectant type associated with identified container is incorrect for use in the treatment of an identified location.

According to the present disclosure, a method monitors treatment of locations of a facility with a disinfectant that is expirable. The method comprises: associating together, in at least one database, first information of a plurality of containers each having a volume for the disinfectant that is fillable repeatedly with the disinfectant for use in the treatment, the first information comprising each first identifier for each container with each volume and each expiration of the disinfectant filled in each container; obtaining, with communication equipment, electronic input at least of each first identifier associated with the containers before use in the treatment; tracking, with processing equipment, the first information using the electronic input; and alerting, with the processing equipment, an issue with the disinfectant in a given one of the containers before the use in the treatment based on the tracking.

The method can involve steps associated with the system outlined above. Additionally, a program storage device having program instructions for controlling a programmable control device can perform the method of monitoring use of a disinfectant according to the steps involved.

The foregoing summary is not intended to summarize each potential embodiment or every aspect of the present disclosure.

BRIEF DESCRIPTION OF THE DRAWINGS

FIG. 6A-6G are example user interface screens for a processing unit of the disclosed system.

FIGS. 7A-7M are more example user interface screens for a filling station of the disclosed system.

FIG. 8A illustrates examples of an NFC label, RFID tag, and a QR code for the disclosed system.

FIG. 8B illustrates a mobile device, such as a smart phone, having a mobile software application operating an NFC device or other reader.

FIG. 11 shows an example room report that may be generated based on stored information of a completed cleaning task.

DETAILED DESCRIPTION

Figure 1:
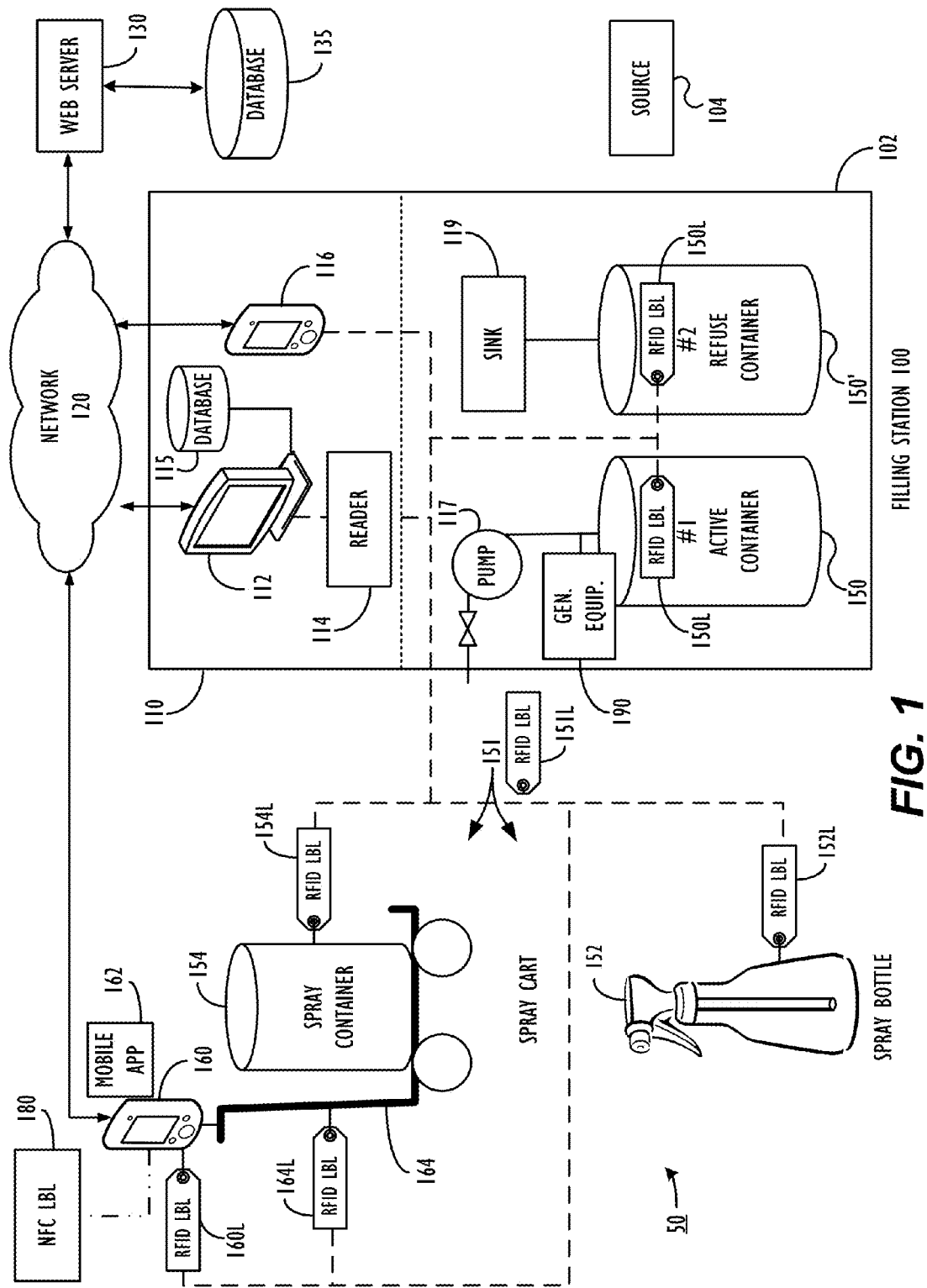
FIG. 1 is a block diagram of a system for tracking a disinfectant from its time of production through its time of use.

Referring to FIG. 1, a system 50 according to the present disclosure tracks a material that has an expiration from the time of manufacture. In general, the material can be a liquid, solid, or gas composition that degrades or otherwise loses its effectiveness, expires, or spoils within a particular time span from its point of production or manufacture. As such, the material has an expiration, meaning that the material has a limited duration of effectiveness, an expiration date, an effective period, a designated shelf life, or the like. For the purposes of discussion, the term "expiration date" may be used for convenience. As noted herein, one particular material suited for the disclosed system 50 includes hypochlorous acid (HOCl), although other disinfectants, agents, natural or man-made materials can benefit from the system 50 of the present disclosure. Indeed, it is even contemplated that the disclosed system 50 can be used with produce, food products, beverages, juice, milk, water, and any other material that is dispensed and has an expiration.

The system 50 includes a filling or distribution station 100, a local control unit 110, a remote control unit 130, various containers 150, 151, 152, and 154, and other components. The filling station 100 and the local control unit 110 are housed in a facility requiring disinfection, such as a hospital, a nursing home, a dormitory, a school, etc. Distribution containers 150 of the expirable disinfectant are delivered to the facility from source locations 104 and are stored at the filling station 100. The dispensing, use, and expiration of the disinfectant is monitored by the local control unit 110, and the remote control unit 130 operates in conjunction with the local control unit 110 to monitor the delivery and use of the disinfectant and operates in conjunction with the source 104 or manufacturer of the disinfectant.

At the facility, the filling station 100 serves as a point of distribution from a distribution container or drum, such as container 150, allowing users to fill and use various dispensing or use containers 151, such as spray bottles 152, cart-transported sprayers 154 (e.g., electrostatic sprayers), hand-sanitizer dispensers, and other devices to disinfect and sanitize the facility. The users can be cleaning personnel, janitors, maids, nurses, doctors, etc.

In the illustrated embodiment, the filling station 100 includes both the local control unit 110, which may include processing equipment, communication equipment, and a user interface, and includes a distribution portion 102. Accordingly, the filling station 100 and the local control unit 110 may be implemented as a kiosk or other integrated unit.

The local control unit 110 serves as a user interface to the filling station 100 and to the system 50 as a whole. Processing and communication equipment of the local control unit 110 may include a computer 112, which can include a user display and peripherals such as a keyboard, mouse, touchscreen monitor, or other input and output devices for interacting with the users and other parts of the system 50. The computer 112 includes a connection to a network 120 that enables system functionality (described in greater detail below). The network connection may take any form including, but not limited to, a local area network (LAN), a wide area network (WAN), such as the Internet, or a combination of local and wide area networks. Moreover, the network 120 may use any desired technology, or combination of technologies (including, but not limited to, wired, wireless, cellular, or a combination thereof) and protocol (e.g., transmission control protocol, TCP).

The processing and communication equipment of the local control unit 110 can further include a reader 114 operatively coupled to the computer 112. The reader 114 actively reads information associated with the various containers 150, 151, 152, 154, etc. used to dispense and hold the disinfectant. Various types of reader 114 can be used, including, but not limited to, a Radio Frequency Identification (RFID) reader, a scanner, a barcode reader, a Quick Response (QR) code reader, or other optical or electromagnetic device. For the purposes of the present disclosure, the reader 114 is referred to as an RFID type of reader for reading RFID tags, labels, and the like. This is meant to provide an example for the purposes of description and is not intended to be limiting.

The processing and communication equipment of the local control unit 110 may additionally include a mobile locator device 116, such as a handheld scanner or reader. While the mobile locator device 116 may typically be docked at the filling station 100, it may be removed from the filling station 100 in order to detect a distribution or use container 150, 151, etc. when necessary as will be described in greater detail below. The mobile locator device 116 may be a mobile device, such as a personal digital assistant, a tablet computer, a mobile telephone, or any other similar device and may execute a software application that provides certain system functionality. Like the computer 112, the mobile locator device 116 may be connected to the network 120. Similarly, the mobile locator device 116 may include a reader (not shown), such as a radio frequency identifier (RFID) transceiver.

In the illustrated embodiment, the distribution portion 102 of the filling station 100 includes locations and plumbing connections for two distribution containers 150 and 150'. The first distribution container 150 is an active filling container that contains effective disinfectant (i.e., material within its effective expiration date) and is used to fill use containers 151 (e.g., spray bottle 152, spray container 154, etc.).

The other distribution container 150' is a refuse container used to collect residual disinfectant from use containers 151 through a filling station sink 119. This refuse container 150' may also receive expired disinfectant directly from the active filling container 150. Accordingly, there may be a plumbing connection (not shown) between the two distribution containers 150 and 150' to enable the transfer of expired disinfectant from the active filling container 150 to the refuse container 150' prior to replacing the active filling container 150 with a new container. Of course, the distribution portion 102 can have more than one active filling container 150 for dispensing the disinfectant.

As shown in FIG. 1, the distribution portion 102 may additionally include instrumentation for managing the materials. For example, the distribution portion 102 may include flow and level measurement devices (not shown) and transfer devices (e.g., pumps 117) for automatically measuring and transferring disinfectant from the distribution container 150 to the use containers 151. As also shown in FIG. 1 but discussed later, the distribution portion 102 may include generation equipment 190 in addition to or instead of the distribution container 150. The generation equipment 190 can be used for generating, creating, or producing the disinfectant at the station 100.

To track and monitor the use and distribution of the disinfectant, each distribution container 150 and each use container 151 includes coded information in a tag, label, or the like affixed to (or otherwise associated with) the container. In the present example, each of the containers 150 and 151 has an attached RFID label that uniquely identifies the container. As is known by those of ordinary skill in the art, RFID labels allow for the wireless transmission of data over relatively short distances. The RFID labels (e.g., labels 150L, 151L, 152L, and 154L) that are attached to the distribution and use containers 150, 151, 152, and 154 may be active RFID tags (powered by a local power source (e.g., a battery)), or they may be passive RFID tags (utilizing the electromagnetic signals emitted by the transceiver as power to respond with their unique identifier).

Figure 2A:
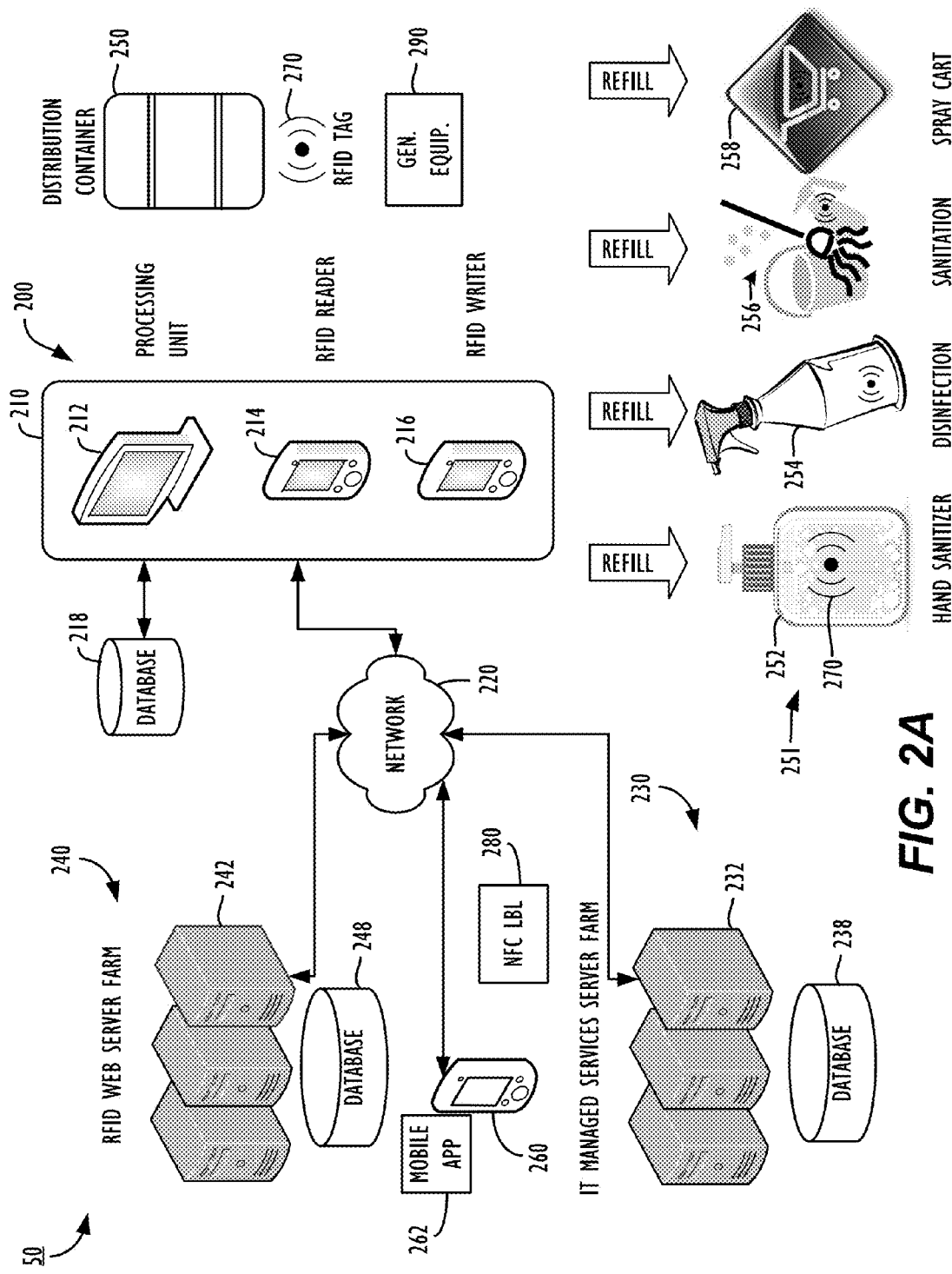
FIG. 2A schematically illustrates a configuration of the system in which equipment at a facility is connected via a network connection to remote services.
Figure 2B:
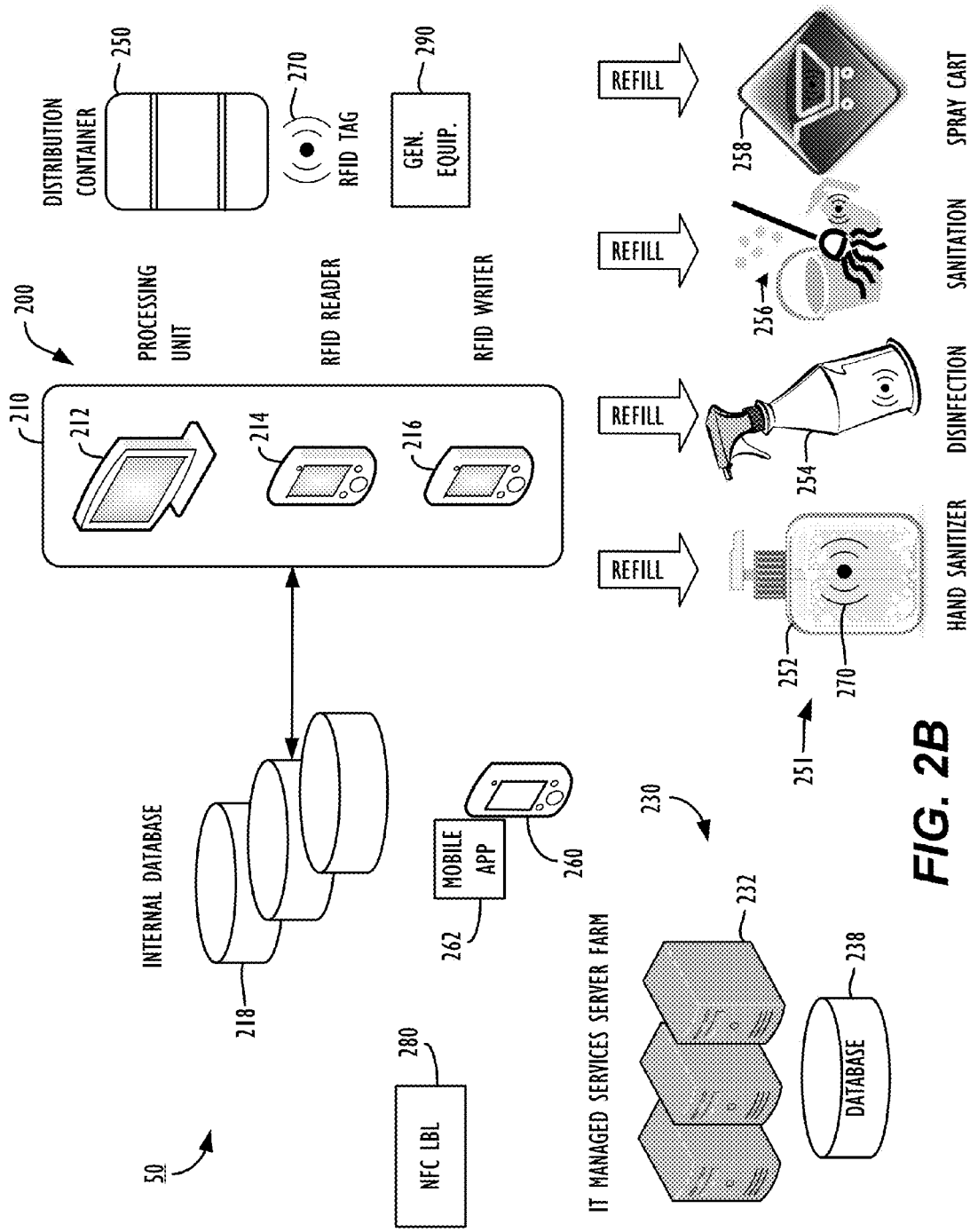
FIG. 2B schematically illustrates a configuration of the system in which the equipment at the facility is not connected via a network connection to remote services.

As will be set forth below, the local control or processing unit 110 of the filling station 100 may execute an application that utilizes the RFID labels 150L, 151L, 152L, etc. to track the location of the disinfectant from the production of the disinfectant at its source 104 through its use at the facility. In one embodiment, the application may be executed as a web-based application with some portion of the program code executing remotely from filling station 100 (e.g., at the web server 130). For example, a database 135 may reside on the web server 130 (or another network device including a database 115 of the personal computer 112) to track the current status of all system distribution and use containers and to track the expiration of the disinfectant those containers have. (FIGS. 2A-2B show arrangements for tracking disinfectant and containers from manufacture through use at a facility.)

The functionality of the disclosed tracking system 50 will now be described by reference to examples from a typical lifecycle for a particular volume of the disinfectant. Initially, the disinfectant, such as hypochlorous acid, is produced at a source 104—i.e., a production/distribution facility. A batch of the disinfectant may be associated with certain properties (e.g., a batch number, a production date, results of standard lab analyses of sample material from the batch, expiration, etc.). An empty distribution container 150 is filled with the newly produced material. The transfer of disinfectant to the distribution container 150 may be performed at a filling station similar to the filling station 100 located at the local facility. (FIG. 3A below discloses a process for filling a distribution container with disinfectant.)

To perform a filling operation, a user may log in through the interface portion of such a filling station 100. In one embodiment, logging in to the filling station 100 may require the entry of a user name and password such that the user may be authenticated. Based on this required authentication, all filling station events may be associated with a particular user. The user may then select an option to initiate the filling operation. In response, the filling station 100 uses the reader 114 to locate any RFID labels 150L that are within communication range. If one or more RFID labels 150L are identified, the user may be asked to select the container 150 that is to be filled from a list of the identified containers 150. For example, the user may read a label 150L from the container 150 and identify a matching label from a list of labels corresponding to the identified RFID labels. In the unusual event that no RFID label is identified by the filling station 100, the user may be prompted to resituate the container 150 such that the RFID label may be identified. If a label is not identified for the container 150 or if the container 150 or label 150L is not recognized, then the user is not instructed to fill the container 150.

Once the container 150 has been selected, the user is prompted to connect the container 150 to begin the filling operation. In one embodiment, the filling station 100 may present an illustration of the necessary plumbing connection (s) to begin the filling operation. Once the connections have been made, the filling operation may be commenced through the filling station interface.

In one embodiment, the system 50 may retrieve known properties for the container 150 (i.e., based on the identified RFID label 150L) in order to perform the filling operation. For example, the identified RFID label 150L may be utilized to search one or more of the databases 115 and/or 135 that contain information for containers (both use and distribution) that are managed by the system 50. The database 135 may be located on a remote device such as the web server 130, and/or the database 115 may be located locally. Using the retrieved properties (e.g., container volume), the filling operation may be performed automatically.

Upon completion of the filling operation, the user may be prompted to disconnect the container 150. The filling station 100 then records the filling operation as a system event, which is then associate the dispensed disinfectant in the container 150. For example, the database 115, 135 can be updated to reflect the properties (e.g., manufacture date, results of lab analyses, expiration date, etc.) of the disinfectant in the distribution container 150.

Now that the container 150 is filled, the source 104 delivers the container 150 to its intended use location (e.g., a hospital, a school, a nursing home, etc.). (FIG. 3B below discloses a process for receiving a distribution container at a facility.) In one embodiment, if the distribution container 150 is not to be immediately placed into use in a filling station 100 at its use location, the mobile locator device 116 of the filling station 100 at the use location can be utilized to detect the arrival of the container 150 at the use location. The arrival of the container 150 at the use location is also recorded as a system event. For example, the mobile device 116 may, upon identifying the RFID label 150L of the delivered container 150, update the local database 115 and may update the remote database 135 via the connection to the network 120. A similar operation may be performed when a distribution container 150 is returned to the production/distribution source 104 so that the location of all system containers 150 can be monitored at any point in time.

After the new container 150 has been delivered to its destination, it is used to replace an empty or expired active filling container 150 in the filling station 100. In order to replace the empty or expired container 150, a user logs into the filling station's local control unit 110 and selects an operation to replace the active container 150. In one embodiment, any remaining material in the active filling container 150 may be transferred to the refuse container 150', and the user may be prompted to transfer the remaining material to the refuse container 150'. In another embodiment, the remaining material may be automatically transferred to the refuse container 150'. For example, in response to the user request to initiate the exchange operation, the local control unit 110 of the filling station 100 may open valves and/or start the pump 117 to transfer the material via a connection between the containers 150 and 150'. Because the current filling container will become the new refuse container, removing any remaining contents will enable the container to accept its full volume in disposed fluids.

When the new container 150 is brought into proximity of the reader's range, the local control unit 110 attempts to identify the RFID label 150L for the new distribution container 150 via the reader 114 (e.g., RFID transceiver). Like the filling operation described above, if one or more RFID labels are identified, the filling station 100 may prompt the user to verify the identity of the new distribution container 150 by selecting a label that is printed on the new distribution container from a list of labels corresponding to the identified RFID labels. In one embodiment, based on the known and previously acknowledged identifiers of the existing distribution containers 150 in the reader's range, their labels may be excluded from the list.

After the new distribution container 150 is identified, the filling station 100 can verify that the new distribution container 150 contains effective material. For example, the filling station 100 can query the database 115, 135 for the properties of the disinfectant in the identified container 150. If the disinfectant in the new distribution container 150 is effective (i.e., the current date is prior to the material's expiration date), the user may be prompted to disconnect the existing distribution containers, to connect the existing active filling container as the refuse container, and to connect the new distribution container 150 as the active filling container. If the disinfectant in the new distribution container 150 is not effective, the user may be prompted to obtain a different distribution container that contains effective material.

The filling station 100 may also prompt the user to send the old refuse container 150' back to the distribution source 104. In one embodiment, these instructions implemented by the local control unit 110 may be site specific. For example, the user may be prompted to move the old refuse container 150' to a particular site location designated for pickup and transportation back to the distribution source 104.

Using the known identifiers of the previous distribution containers and the identified RFID label 150L for the new active filling container 150, the filling station 100 records the events. Recording the events may include updating the database 115, 135 to reflect the new status for each of the distribution containers 150. In one embodiment, the filling station 100 may also schedule one or more future events. For example, based on the known properties of the disinfectant in the new active filling container 150, an alert may be scheduled to occur on or near the expiration date of the material in the new active filling container 150 if it is still being used as an active filling container 150 on the expiration date (or some time period prior to that date).

Now that the filing station 100 has disinfectant, the station 100 can be used to dispense the disinfectant from the active filling container 150 to the various use containers 151. To do this, a user logs in to the filling station 100 and selects a dispense operation from the interface. (FIG. 3C below discloses a process for filling a use container with disinfectant.) In response to the selection, the filling station 100 attempts to identify any RFID labels 151L for use containers 151, such as label 152L for spray bottle 152 or label 154L for cart-mounted spray tank 154, that the user brings to the reader 114. In one embodiment, a cart 164 and a near field communications (NFC) reader, another RFID reader, or other type of reader or mobile device 160 may additionally have RFID labels 164L and 160L, respectively, that can be read to associate the use container 151 with these devices at the time of a dispense operation.

Just as with the previous operations, if one or more RFID labels are detected, the user may be prompted to verify a label printed on the use container 151 to be filled by selecting the label from a list of labels corresponding to the identified RFID labels. In one embodiment, because the system 50 is aware of the type of container 151 associated with each RFID label, the labels for distribution containers 150 are excluded from the list. Once the use container 151 has been identified and selected, the user is prompted to specify the volume of disinfectant that remains in the use container 151, and, if any disinfectant remains, to dispose of the remaining disinfectant in the filling station sink 119 for the refuse container 150'.

The user is then prompted to connect the use container 151 to the active filling container 150. In one embodiment, the use container 151 may be filled automatically. For example, the volume of the use container 151 is retrieved using the RFID label 151L of the use container 151, and the appropriate volume is transferred from the active filling container 150 to the use container 151 using the various pumps 117, valves, and the like of the filing station 100. Alternatively, the user is prompted to manually fill the use container 151.

After the use container 151 is filled, it is disconnected from the active filling container 150. The system 50 then records the filling of the use container 151 as an event. Recording the event includes updating the database 115 and/or 135 to reflect the contents of the filled use container 151, the amount of disinfectant dispensed to that container 151, the expiration date of the dispensed disinfectant in that container 151, and the association of the use container 151 with other devices (e.g., cart 164 and NFC reader or mobile device 160). In other words, because the system 50 is aware of the properties (e.g., a batch number, a production date, results of standard lab analyses of sample material from the batch, expiration, etc.) of the disinfectant in the active filling container 150, these properties can be transferred to the filled use container 151.

The system 50 can also schedule future events based on the filling operation. For example, an alert can be created to occur on the expiration date of the material if the use container 150, 155 has not been returned for refill prior to that date. In one embodiment, when an alert is generated indicating that a use container 151 contains material that is beyond its effective date, a user may be prompted to use the mobile locator device 116 to locate the use container 151 and bring it to the filling station 100 to empty the expired contents.

As noted above, recording the filling operation can also include recording a transferred volume. In one embodiment, the transferred volume is based on a measured amount of transferred material (e.g., measured using a flow measurement device or using a measured volumetric change in the active filling container 150). In another embodiment, the volume is estimated based on the known properties of the filled use container 151. In either case, the recorded volume transferred in accordance with the filling operation can be used to track the actual yields of the active filling container 150 against its expected yield (e.g., by creating reports or alerts associated with the yield).

The utilization of a particular use container 151 to perform a treatment in the facility can also be tracked by the system 50. In the embodiment illustrated in FIG. 1, the cart-mounted spray tank 154 is associated with an NFC device 160, although the reader device 160 can be another RFID reader, an optical reader, or any other type of reader as disclosed herein. NFC reader device 160 may be a mobile device such as a personal digital assistant, a tablet computer, a mobile telephone, or any other similar device and may be connected to the network 120 (e.g., via a wireless network connection) and can operate using a mobile application 162. The NFC reader device 160 can be attached to the spray cart 164 and can be removable so the NFC reader device 160 can be used to read an NFC label 180 to indicate the performance of a treatment. In one embodiment, the NFC reader device 160 is connected to the spray cart 164 via a retractable connector that allows the NFC reader device 160 to be placed in close proximity to the NFC label 180. For its part, various NFC labels 180 can be mounted in areas that are commonly treated (e.g., hospital rooms, etc.) and can uniquely identify the area in which they are mounted so that performance of tasks related to these areas can be monitored by the system 50. In this way, the system 50 can track which dispensed material, along with its expiration date, source information, etc., was used to clean an area of the facility and can track what task (e.g., type of treatment) was performed. Additional information associated with the user, the equipment, time, date, and the like can also be correlated with these details.

For example, prior to treating a monitored area, a user places the NFC reader device 160 associated with the use container 151 (e.g., spray container 154) that will be used to treat the area in close proximity to the NFC label 180 for the area to be treated. In addition, the user may be required to enter user authentication credentials through the mobile application 162 of the NFC reader device 160. The system 50 may only allow an NFC reader device 160 to be "scanned in" to a single location at any time. That is, once an NFC reader device 160 has been used to signify the beginning of a treatment at a particular area, the reader device 160 must be used to signify the end of the treatment of that area before the reader device 160 can be used at another area. Otherwise, the system 50 may generate an appropriate alert.

Because the NFC reader device 160 is associated with the use container 151, it can be determined whether the material in the use container 151 is effective. If the disinfectant is not effective, the user may receive an alert to the expiration and may be prompted to return to the filling station 100 to obtain effective disinfectant. If the disinfectant is effective, the user may be prompted to perform the treatment. The use container 151 can then be utilized to dispense the disinfectant in the monitored area (e.g., using an electrostatic spray device).

After the treatment has been performed, the user again brings the NFC reader device 160 into close proximity of the NFC label 180 to signify completion of the task. The NFC reader device 160 may transmit information via the network 120, and the system 50 may then record a use event that associates the area treated with the user that performed the treatment, the use container 151 used to perform the treatment, and the properties of the material in the container 151 used to perform the treatment.

In one embodiment, recording the use event may include marking a scheduled task (e.g., a task to treat a certain area) as complete. In such an embodiment, credit may only be given for the completion of a task when the proper procedures have been followed (e.g., using the NFC reader device 160 to record the task) so that the effectiveness of the disinfectant used can be verified.

In another embodiment, credit may only be given for a scheduled task when the use container 151 is returned to the filling station 100. In such an embodiment, credit may only be given where a dispensed volume exceeds a volume associated with the task. For example, if a use container 151 that was recorded as having been used to perform a treatment is returned to the filling station 100 with a residual volume that indicates the dispensed volume was less than an amount required for the performed treatment, the scheduled task may not be marked as complete, and the user may be prompted to perform the task again. In such an embodiment, the material volume associated with the task may be a default volume associated with the particular area. Alternatively, the material volume associated with a task may be adjustable using a system interface. For example, to treat an area that was recently used by a patient having a certain infection, the material volume associated with the task may be increased.

The described system 50 provides a mechanism for ensuring that a disinfectant used to perform a treatment is within its effective period. In addition, because each filling station 100 may be connected to the Internet via the network 120 with at least a portion of the system's functionality implemented as a web application, system monitoring may be performed remotely. For example, using an Internet-connected device, the system 50 may be accessed in order to retrieve desired system statistics. These statistics may be presented in user-created or predefined reports having varying levels of detail.

FIG. 2A schematically illustrates a configuration of the system 50 in which processing equipment 210 of a filling station 200, unit or the like at a facility is connected via a network connection 220 to remote services, including a managing source 230 and a tracking source 240. Although shown separate, the managing source 230 and the tracking source 240 may be one and the same entity, but they are described separately for purposes of understanding.

The system 50 includes processing and communication equipment, including processing equipment 210, processing unit 212, readers 214, mobile devices 260, mobile applications 262, user interfaces, servers 230 and 240, communication interfaces (not shown) and the like. The processing and communication capabilities of the equipment of the system 50 can be shared between the various components. In addition to this equipment, the system 50 includes at least one database (e.g., 218, 238, 248, etc.) associating various pieces of information together for the purposes disclosed herein.

The system 50 includes first identifiers 270 (e.g., readable devices, RFID tags, NFC labels, etc.) that are electronically readable and are associated with a plurality of containers (250, 251, etc.) each having a volume that is fillable repeatedly with the disinfectant for use in the treatment. The system 50 also includes second identifiers 280 (e.g., readable devices, RFID tags, NFC labels, etc.) that are electronically readable and are associated with the locations for the treatment with the disinfectant.

The processing equipment 210 at the facility may store information locally in local databases 218 and may upload and download information for storage with the sources 230, 240. Also, the processing equipment 210 may not store at least some forms of information locally and may instead access that information from the sources 230, 240 as needed via the network connections 220.

The managing source 230 has servers 232 and databases 238 and may be responsible for one or more activities, such as manufacturing, ordering, and distributing the expirable disinfectant; billing the facility; and other types of management services. The tracking source 240 also has servers 242 and databases 248. This source 240 may be responsible for activities, such as tracking containers, storing tracked information, monitoring usage and events, etc. Although shown connected to the processing equipment 210 at one facility, these sources 230 and 240 can operate in conjunction with multiple facilities having processing equipment 210.

In this system 50 similar to the activities disclosed above, containers, such as distribution container 250 and use containers 251 (e.g., hand-sanitizer dispensers 252, disinfection dispensers 254, sanitation dispensers 256, spray carts 258, etc.) are brought to the equipment's reader 214 (e.g., the container's RFID tag 270 is brought within range of the RFID reader 214, the container's barcode 270 is read by the optical reader 214, etc.), the processing equipment 210 detects the container 250-258, and the fluid dispensing process may begin. The processing equipment 210 allows users to refill each container 251 and reassign or tag the fluid expiration date associated with the dispensed fluid. When the expiration date on a container 250-258 is met, the processing equipment 210 alerts the users to refill and retag the container 250-258 to ensure the fluid's potency and effectiveness.

As shown, a particular distribution container 250 at the facility having the processing equipment 210 may be nearing its expiration date, and the system 50 monitors the expiration dates of the various containers 250-258 stored in the equipment's local database 218 and/or in one or more remote databases 238, 248. The system 50 sends a communication (e.g., email, text, SMS, etc.) to a user and may display a notification window on a user interface screen of a computer, a Kiosk, a tablet, a laptop, or other processing unit 212. To send the communications, the processing equipment 210 may originate the communication, or the tracking source 240 may do this.

The user then orders a new distribution container 250 at the processing unit 212, although other channels for ordering could be used. In turn, the processing unit 212 sends the order request to a source 230, which may or may not be the actual manufacturer of the expirable disinfectant. The source 230 can be a distributor, a service provider, etc. that manages services for the facility.

The source 230 then ships a new distribution container 250 to the facility, and the user eventually receives the new distribution container 250 and replaces any expired distribution container 250 at the facility. Although one distribution container 250 is shown, a facility may have multiple distribution containers and may have multiple stations 200 with processing equipment 210 interconnected via the network 220 or other local connection. Preferably, the processing equipment 210 detects the new distribution container 250 when it is set up at the filling station 200 of the facility or when a user logs the distribution container 250 in at the facility. The processing equipment 210 records its expiration date and fluid levels, among other possible details, such as location, arrival date, manufacturer, etc. Once this is done, the new distribution container 250 is ready for use to dispense the expirable disinfectant. As also shown in FIG. 2A but discussed later, the filling station 200 may include generation equipment 290 in addition to or instead of the distribution container 250. The generation equipment 290 can be used for generating, creating, or producing the disinfectant at the station 200.

During use for dispensing, various transportable containers 251 are brought to the filling station 200 and the distribution container 250 to obtain expirable disinfectant and to dispose of expired or residual disinfectant. In addition to monitoring the distribution container 250, the system 50 monitors the various containers 251 in use, as they are filled, emptied, discarded, etc. For example, the processing equipment 210 determines that a disinfection bottle 254 contains (or is expected to contain) disinfectant nearing its expiration date. The system 50 (e.g., tracking source 240 and/or processing equipment 210) sends a communication (e.g., email, text, SMS, etc.) to the user and displays a notification window on the equipment's processing unit 212.

The user returns the disinfection bottle 254 to the processing equipment 210 and launches a dispenser program on the processing unit 212 to begin a refill operation. The reader 214 of the equipment 210 detects the disinfection bottle 254, and the processing unit 212 instructs the user to dispose of expired disinfectant (if any) and dispense new disinfectant into the container 254. The processing unit 212 records how much disinfectant is disposed of and dispensed with, and the processing unit 212 updates the databases 218, 238, 248 (locally and/or remotely) with a new expiration date for the container 254 and its newly dispensed contents. For example, the disposal of the old disinfectant and the dispensing of the new disinfectant are saved as events to the unit's internal database 218, and the events are also sent in separate or batch uploads to the tracking source's database 248 via the network connection 220.

In some implementations, the processing equipment 210 at the facility may be unconnected to the various remote sources 230 and 240. For example, FIG. 2B schematically illustrates a configuration of the system 50 in which the processing equipment 210 at the facility is not connected via a network connection to remote services. As before, the system 50 includes processing and communication equipment, including processing equipment 210, processing unit 212, readers 214, mobile devices 260, mobile applications 262, user interfaces, servers 230, communication interfaces (not shown), and the like. The processing and communication capabilities of the equipment of the system 50 can be shared between the various components. In addition to this equipment, the system 50 includes at least one database (e.g., 218, 238, etc.) associating various pieces information together for the purposes disclosed herein.

The system 50 includes first identifiers 270 (e.g., readable devices, RFID tags, NFC labels, etc.) that are electronically readable and are associated with a plurality of containers (250, 251, etc.) each having a volume that is fillable repeatedly with the disinfectant for use in the treatment. The system 50 also includes second identifiers 280 (e.g., readable devices, RFID tags, NFC labels, etc.) that are electronically readable and are associated with the locations for the treatment with the disinfectant.

When containers 250-258 are brought to the equipment's reader 214, the processing unit 212 detects the container 250-258 so the fluid dispensing process may begin. Again, the processing unit 212 allows the user to refill each container 250-258 and retag the fluid expiration date. When the expiration date on a container 250-258 is met, the processing unit 212 alerts the user to refill and retag the container 250-258 to ensure the fluid's potency and effectiveness.

During the course of operation, the currently used distribution container 250 may be nearing its expiration date. The processing unit 212 sends a communication (e.g., email, text, SMS, etc.) to the user and displays a notification window on the unit's user interface. The user then orders a new distribution container 250 through other channels. When the order is received by the managing source 230, a new distribution container 250 is shipped to the facility. The user receives the new distribution container 250 and replaces the expired distribution container 250. The processing unit 212 detects the new distribution container 250, and the user enters the expiration date and fluid levels, among other possible details. At this point, the new distribution container 250 is ready for use. As also shown in FIG. 2B but discussed later, the filling station 200 may include generation equipment 290 in addition to or instead of the distribution container 250. The generation equipment 290 can be used for generating, creating, or producing the disinfectant at the station 200.

During use for dispensing, various transportable containers 251 are brought to the filling station 200 to obtain expirable disinfectant and to dispose of expired disinfectant. The processing unit 212 monitors the various containers 251 in use, as filled, as emptied, etc. For example, the processing unit 212 determines that a disinfection container 254 has disinfectant nearing its expiration date. The processing unit 212 sends a communication (e.g., email, text, SMS) to the user and displays a notification window on the unit's user interface. The user returns the container 254 to the filling station 200 and launches a dispenser program on the processing unit 212 to begin refill. The processing unit 212 detects the returned container 254, and instructs the user to dispose of the expired fluid and dispense new fluid. The processing unit 212 records how much fluid is disposed and is dispensed and updates the local database 218 with a new expiration date. Being untethered from monitoring services, the processing unit 212 saves the various events and other tracking information to the unit's internal database 218.

Figures 3A, 3B:
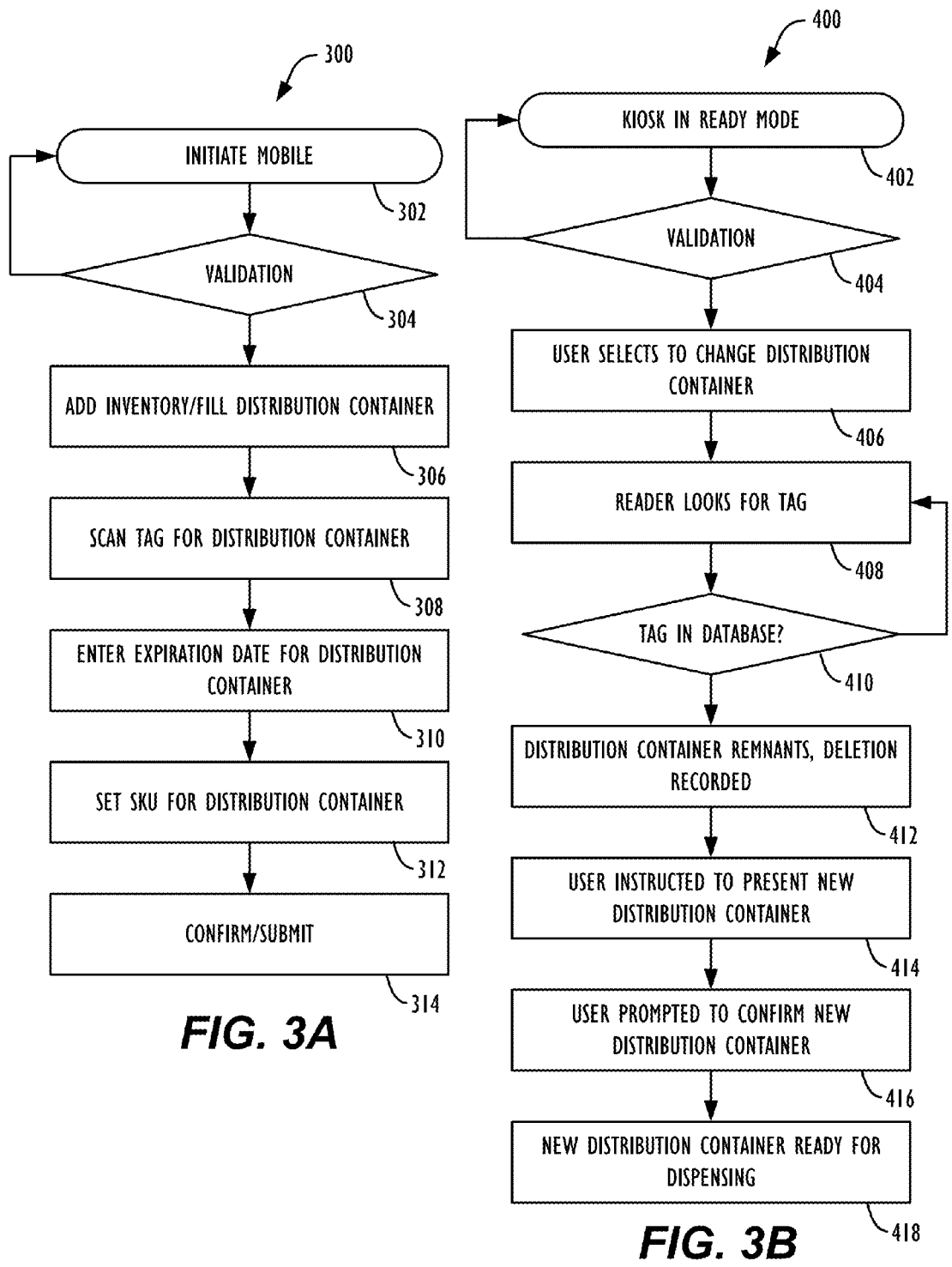
FIG. 3A is a flow chart of a process for tracking a disinfectant from its time of production through its time of use.
FIG. 3B is a flow chart of a process for a user to add or replace distribution containers of the disinfectant at a facility.

As noted above, tracking the disinfectant involves entering tracking information at a source when filling a distribution container with new disinfectant. As an example, FIG. 3A shows a process 300 for filling a distribution container (250) with disinfectant at a source (e.g., managing source 230) and recording its details for later tracking. The process initiates, and a validation step is performed (Blocks 302-304). The user selects to add inventory and fill a new distribution container (250) with the expirable disinfectant (Block 306). The tag for the distribution container (250) is scanned (Block 308). For example, an RFID tag (270) for the distribution container (250) can be scanned. The tagged information may be coordinated with the tracking source (240) if a separate entity.

An expiration date for the new disinfectant is entered into the system (50) (Block 310). The user then sets the stock keeping information (e.g., SKU) for the distribution container (250), indicating the type of container, its volume, its ingredients, its batch number, etc. Finally, the user confirms and submits the entered information for the distribution container (250) so that it can be shipped out to a facility to fill an order (Block 314).

As noted above, tracking the disinfectant involves entering tracking information at a facility when receiving a new distribution container (250). As an example, FIG. 3B shows a process 400 of a user replacing an old distribution container (250) with a new distribution container (250) at a facility. While the processing unit (212) is in ready mode, the user enters access details, and the process goes through a validation step (Blocks 402-404). The user selects to change the distribution container (250), and the reader (214) looks for the tag (270) associated with distribution container (250) in the vicinity of the processing unit (212) that has been used to dispense disinfectant (Blocks 406-410). The processing unit (212) continues to scan for a nearby tag (270) with information stored in the database. When the distribution container (250) is scanned, the processing unit (212) prompts the user to enter what percentage of the distribution container (250) still contains unused disinfectant (Block 412). To maintain consistency in the material disposed, the processing unit (212) instructs the user to dispose of the unused disinfectant.

The user is instructed to present a new distribution container (250) with new disinfectant (Block 414), which is scanned as noted herein. Once the new distribution container (250) is detected or logged, the user is prompted to confirm the new distribution container (250) (Block 416). Once these steps are completed, the new distribution container (250) is ready for dispensing (Block 418).

Figure 3C:
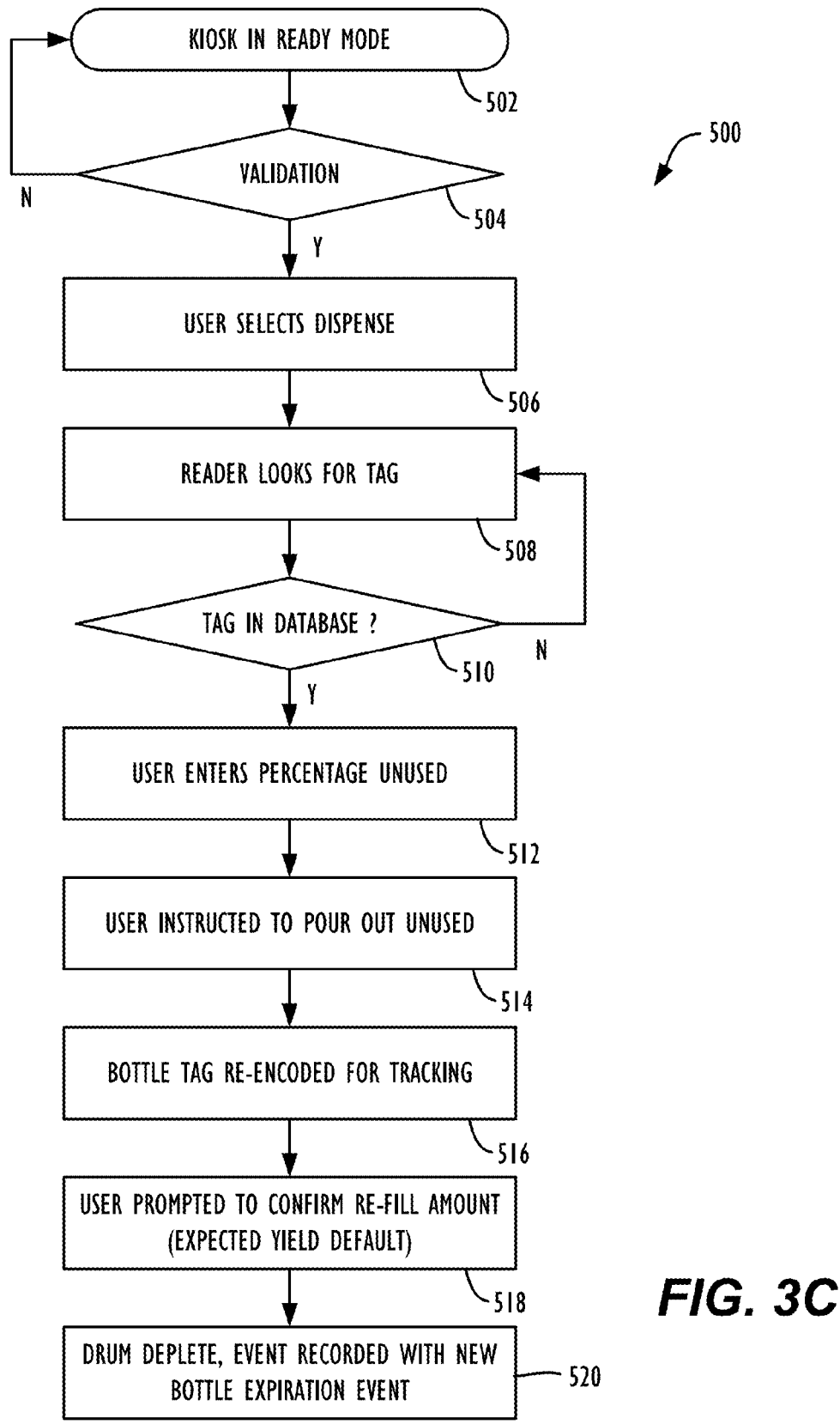
FIG. 3C is a flow chart of a process for a user to empty the container of expired disinfectant, refill the container with a new disinfectant and record onto the identifier of a given container a new expiration date.
Figure 6A:
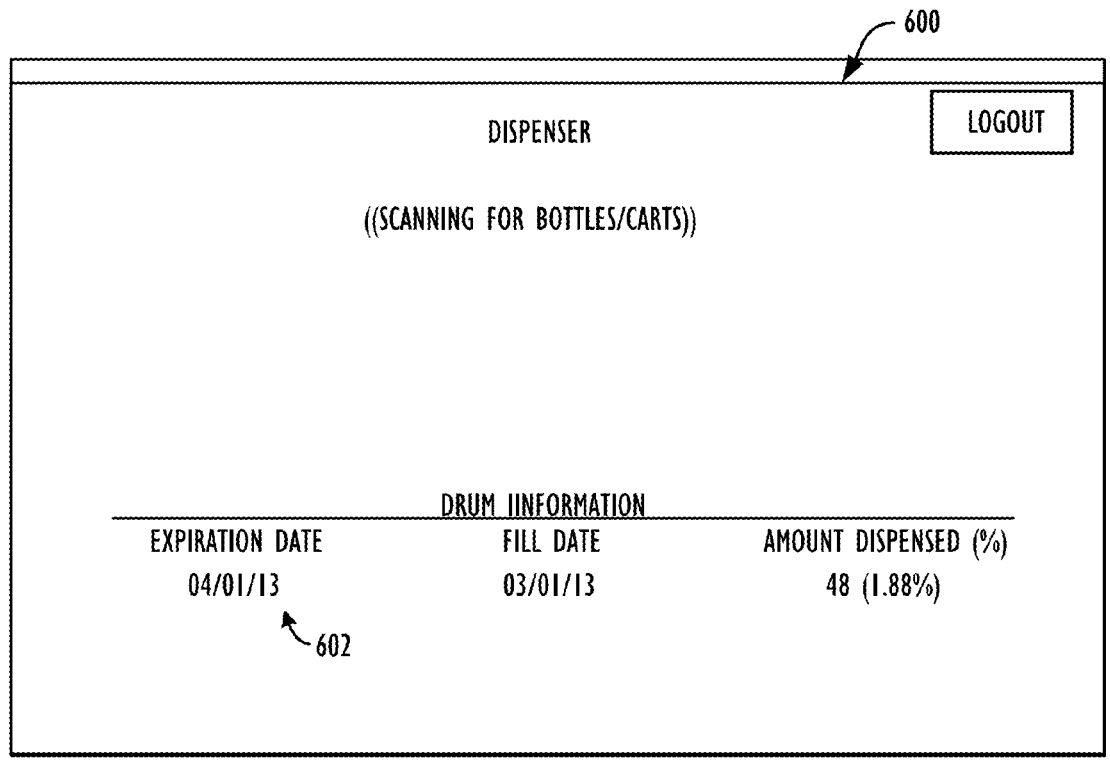

As noted above, tracking the disinfectant involves entering tracking information at a facility when filling user containers (251) with disinfectant. As an example, FIG. 3C shows a process 500 of a user filling a use container (251) at a facility with disinfectant. While the processing unit (212) at the facility is in ready mode (Block 502), the user enters access details, and the process goes through a validation step (Block 504). Having a use container to be used for disinfecting, the user selects to dispense disinfectant with the user interface of the processing unit (212). The reader (214) looks for a tag (270), label, or the like associated with a use container (251) in the vicinity of the unit (212) that the user has brought to be filled. The processing unit (212) continues to scan for a nearby tag (270) with information stored in the database (Blocks 508-510). (FIG. 6A shows an example user interface screen 600 of the processing unit (212) scanning for containers.)

Figure 6B:
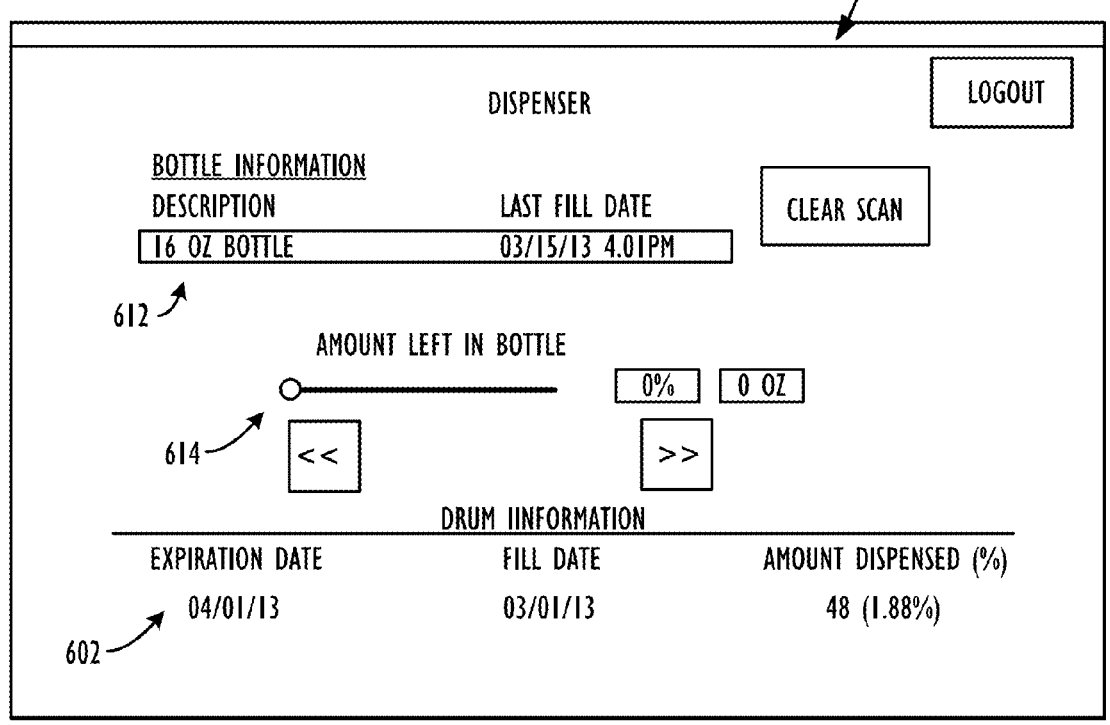
Figure 6C:
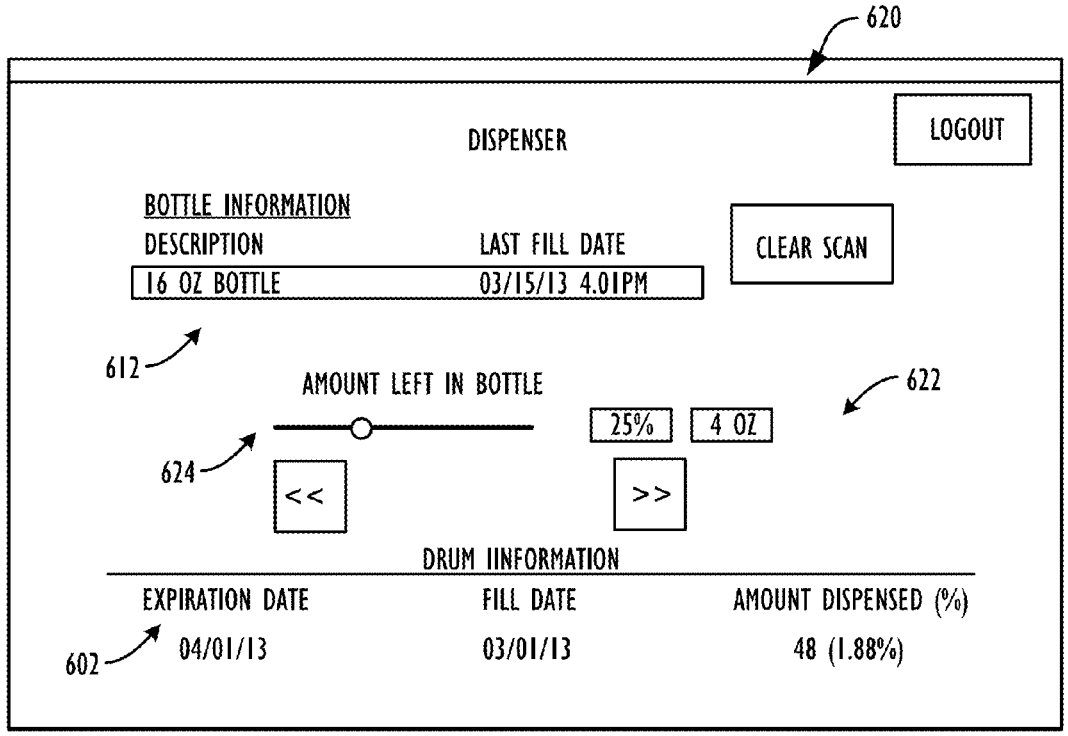

When the use container (251) is scanned, the processing unit (212) prompts the user to enter what percentage of the use container (251) still contains unused disinfectant (Block 512). (FIGS. 6B-6C show example user interface screens 610-620 of the processing unit (212) prompting the user to enter an amount of disinfectant left in the use container (251).) To maintain consistency in the disinfectant dispensed, the processing unit (212) instructs the user to dispose of the unused disinfectant (Block 514).

Once this is done, the container's tag (270) is re-encoded for tracking (Block 516), and the user refills the use container (251) with new disinfectant having its known expiration. When re-encoding the tag (270), the processing unit (212) may use the writer (214) to provide a new RFID for the container (251). Alternatively, however, the RFID of the tag (270) is not rewritten. Instead, the information associated with the particular RFID is merely updated in the databases (218, 238, and 248) of the system 50.

Figure 6D:
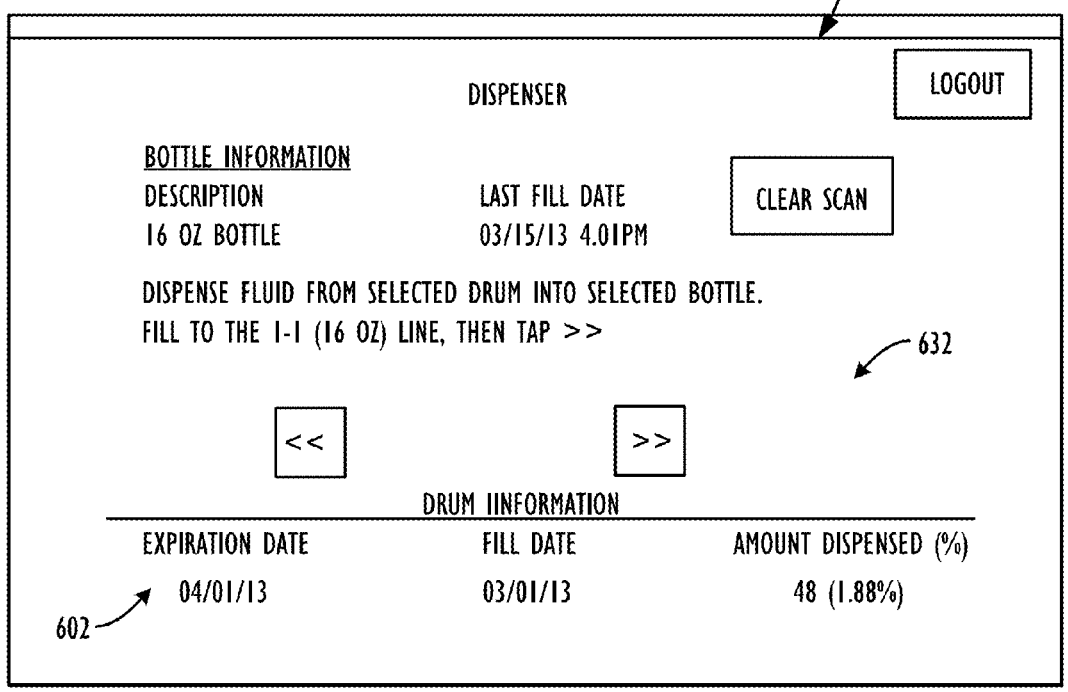
Figure 6E:
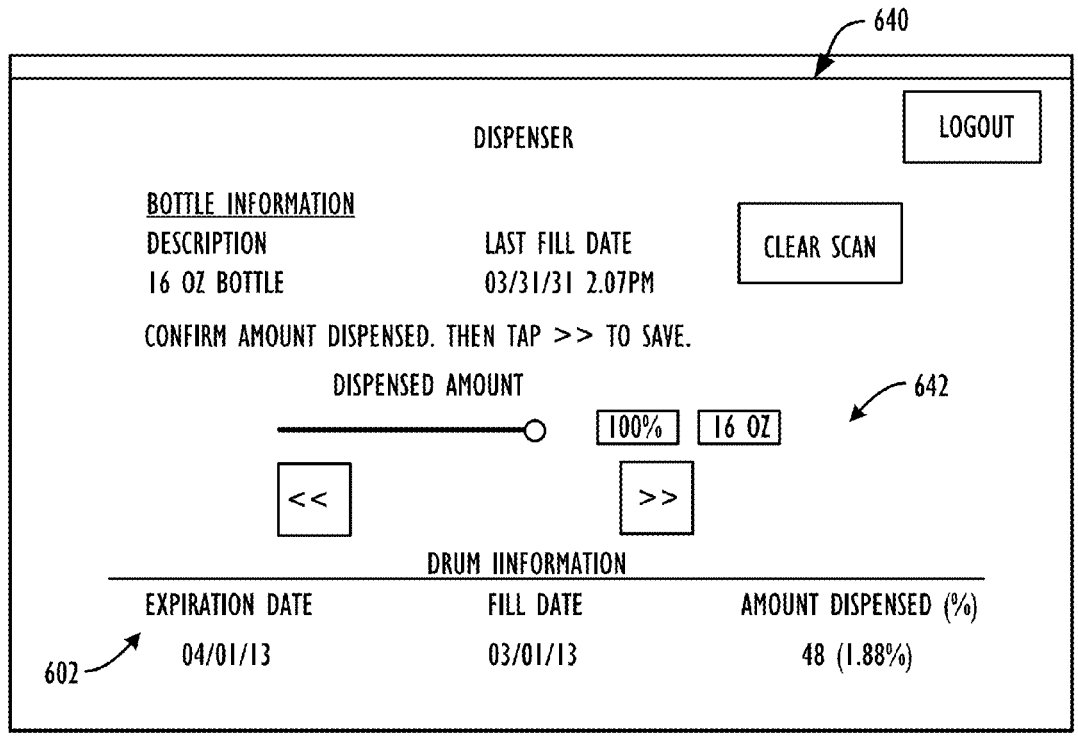
Figure 6F:
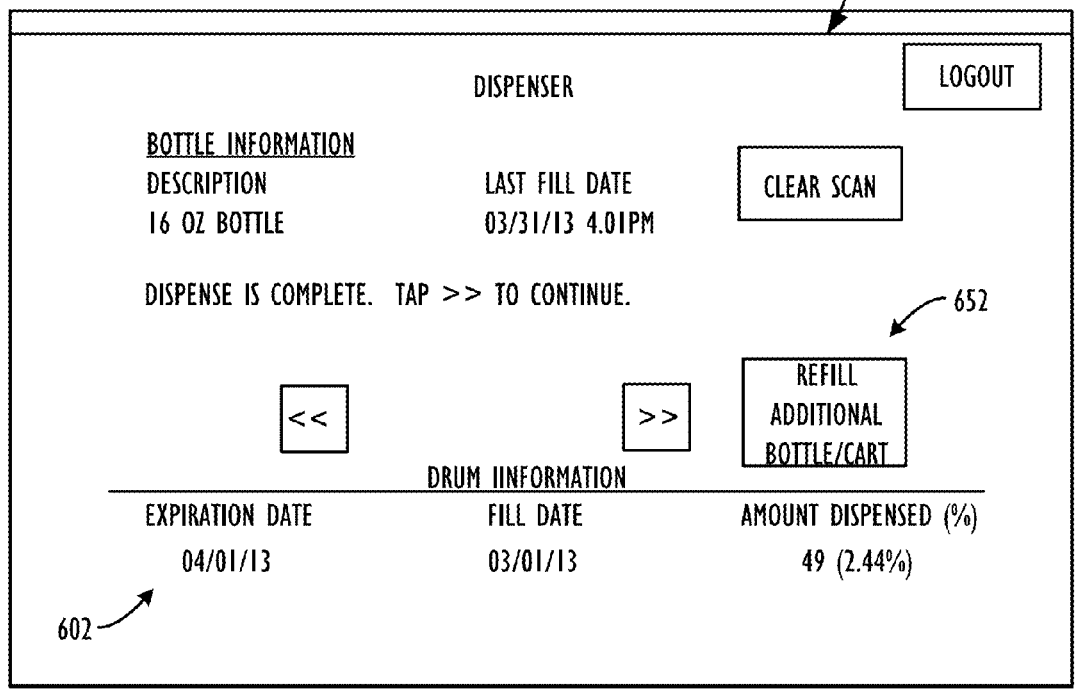

The user is then prompted to confirm what re-fill amount has been dispensed (Block 518). (FIGS. 6D-6F show example user interface screens 630-650 of the processing unit (212) prompting the user to confirm the amount dispensed into the use container.) These steps are repeated as the user brings use containers (251) and until the distribution container (250) is depleted. Once the distribution container (250) is depleted, the event is recorded with a new expiration event.

Figures 4A, 4B, 5A, 5B:
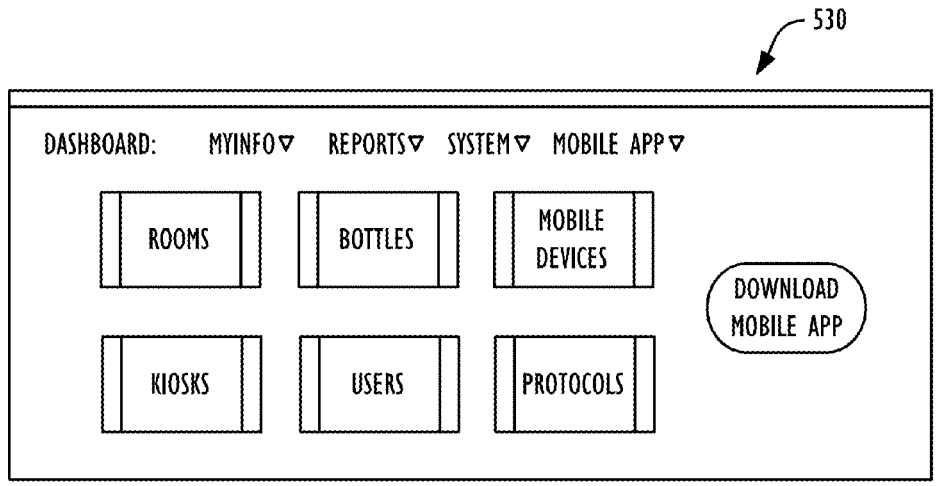
FIGS. 4A-4B are example user interface screens for accessing information in the database(s) of the disclosed system.
FIGS. 5A-5B are example tables of information in the database(s) of the disclosed system.

FIGS. 4A-4B are example user interface screens 530, 540 for accessing information in the database(s) of the disclosed system. A dashboard screen 530 in FIG. 4A shows access to several storage areas in the database(s) of the system. Although wide access may be provided, users at a given facility may access local information about a particular facility. In general, these storage areas can include rooms of the facility, containers (i.e., bottles) used for cleaning, mobile devices used at the facility, kiosks at the facility for dispensing disinfectant, users of the system at the facility, and protocols for types of cleaning to be performed for locations and items at the facility. Various pieces of useful information for tracking these different areas can be stored in the database(s) for interrelation to one another.

For example, FIG. 4B shows an interface of containers (i.e., bottles) of the system stored in the database(s). As shown, the database(s) can store and provide access to information, such as serial number, identifier (e.g., RFID), container type, last fill date, last fill location, etc. of the bottles. A particular bottle can be selected to have a report run on its history. As will be appreciated, each of the storage areas in FIG. 4A can have interfaces such as this for accessing tables of information for the rooms, mobile devices, kiosks, users, and protocols so reports can be produced.

In tracking the containers and their use, the system can track a number of events and other activities. For example, FIG. 5A is an example table of bottle information in the database(s) of the disclosed system. Events, such as bottle commissioning, bottle checks, bottle refills, and the like, can be tabulated in time and location and associated with the bottle identifiers (e.g., RFIDs).

In another example, FIG. 5B is an example table of cleaning information in the database(s) of the disclosed system. Events, such as types of cleaning, can be tabulated in time and location and associated with the bottle identifiers (e.g., RFIDs) of the bottles used. The locations can be at the facility and can be hallways, rooms, and the like. The cleanings of the particular locations can be associated with particular protocols or steps required. The protocols or steps can indicate a certain item to be cleaned, a certain type of cleaning to be done, etc. needing completion. Items to be cleaned in defined steps can include water fountains, hand rails, light switch plates, door plates, trash, sinks, etc. A given cleaning protocol for a room or other location may require several steps to be completed. Some of these steps may require the user to collect data of the step's completion as well as to collect information about the number of items cleaned, such as the number of sinks, trash cans, etc. cleaned in the room.

As noted above, FIG. 6A shows an example user interface screen 600 of the processing unit (212) scanning for use containers (251). On this dispenser screen 600, information 602 about one or more of the existing distribution containers (250) for dispensing the expirable disinfectant is displayed. For example, the information 602 can include the expiration date of the disinfectant in the distribution container (i.e., the date the distribution container was filled (i.e., its disinfectant manufactured), and the amount of the disinfectant already dispensed. As will be appreciated, other information could be tracked and provided.

As noted above, FIGS. 6B-6C show example user interface screens 610-620 of the processing unit (212) prompting the user to enter an amount of disinfectant left in a use container (251) when bringing the use container to be filled. Having scanned for the use container, the processing unit (212) obtains recorded information about the use container and displays some of the container details 612. For example, the scanned use container (251) shown in FIG. 6B is a 16-oz spray bottle.

User input elements 614 allow the user to indicate the amount of unused disinfectant contained in the use container (251). As shown on the screen 620 in FIG. 6C, for example, the user can enter the percentage and/or ounces left in the container (251) using a slider 624 and/or manual input 622. Because the volume of the use container (251) is known and tracked, entering this information can be accurate to the extent needed.

Once the excess disinfectant has been discarded, the user can then dispense new disinfectant from the associated distribution container (250) into the now empty use container (251). As noted above, FIGS. 6D-6F show example user interface screens 630-650 of the processing unit (212) prompting the user to confirm the amount dispensed into the use container (251). In FIG. 6D, instructions 632 are displayed to the user to dispense the new disinfectant from the associated distribution container (250) into the respective use container (251). As disclosed herein, this can be a manual process in which the user operates a manual pump to draw the disinfectant from the distribution container (250) and visually fills the respective use container (251) to the proper fill line. Alternatively and as also noted previously, this process can be automated at the filing stations 200 using pumps, valves, and sensors.

The user can then be prompted to confirm the amount dispensed as shown in the screen 640 of FIG. 6E. Then, as shown in FIG. 6F, the information 602 about the distribution container (250) may be appropriately updated to track the amount dispensed and estimate the amount remaining in the distribution container (250).

During operations, the processing unit (210) can be used to generate reports, track how much disinfectant is expected to be present and dispensed in use containers, and perform other functions. FIG. 6G shows an example interface screen 660 of the processing unit (212) for generating reports. Various search criteria, categories, and the like 622 can be selected for generating a report, and the reported information can be displayed in tabular form 664 for review and potential export.

Figure 7:
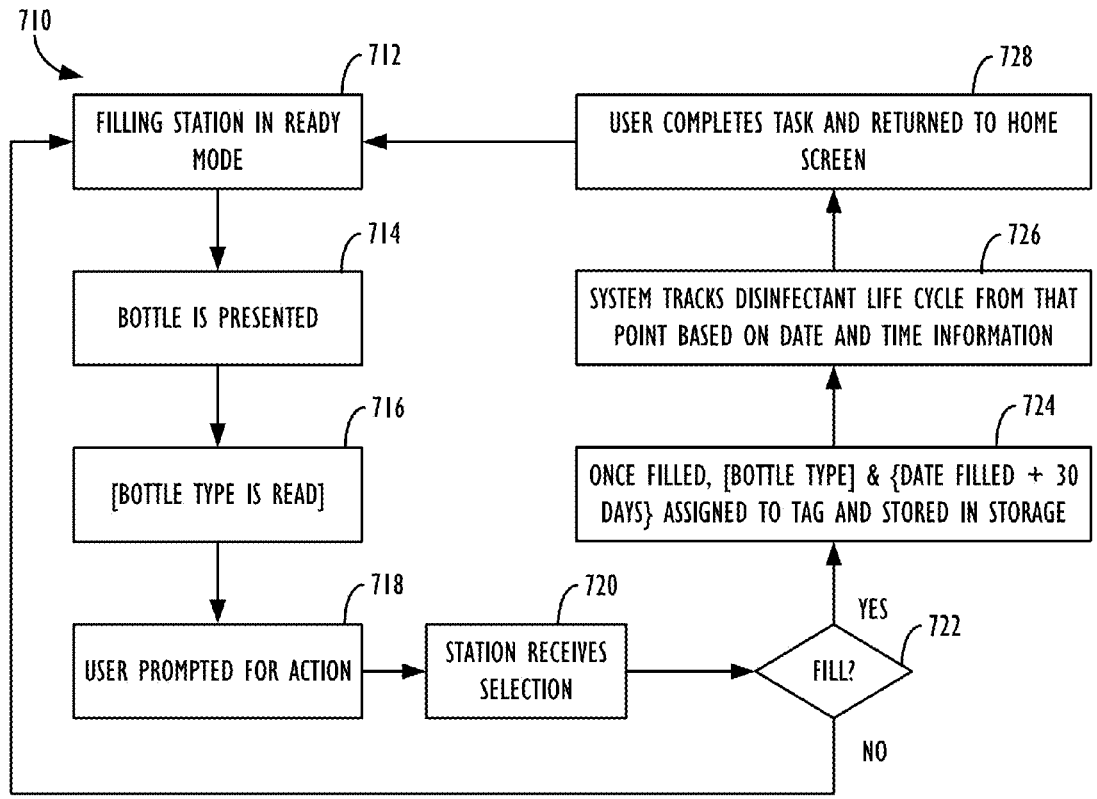
FIG. 7 illustrates a workflow according to one embodiment of the present disclosure.

FIG. 7 illustrates a workflow of a filing station 100, 200 or processing unit 110, 210 of the system 50 according to one embodiment of the present disclosure. Meanwhile, FIGS. 7A-7M are more example user interface screens for the filing station 100, 200 or processing unit 110, 210 of the disclosed system 50. According to the present disclosure, a processing unit (e.g., 110: FIG. 1, 210: FIGS. 2A-2B) can be part of a filling station (e.g., 100: FIG. 1, 210: FIGS. 2A-2B) for dispensing and optionally disposing of the disinfectant. The dispensing can be made from a distribution container (e.g., 150: FIG. 1, 250; FIGS. 2A-2B) or other source (e.g., generation equipment 190, 290). The disinfectant can be delivered to the station (110, 200) and/or can be generated, created, or produced at the station (110, 200) depending on the type of disinfectant used. (As noted previously, the system 50 in FIGS. 1 and 2A-2B includes generation equipment 190, 290 for generating, creating, or producing the disinfectant at the station 100, 200 in addition to or instead of the distribution container 150, 250.) Moreover, various types of disinfectant may be available from the filling station (110, 200) at the same time.

The generation equipment 190, 290 of the system 50 can produce a variable ppm solution. For example, the disinfectant can include a 500-ppm Hypochlorous acid (HOCl) solution created at the station (100—i.e., with the generation equipment 190) or elsewhere through an electrolytic process of Electro-Chemical Activation, which involves temporarily modifying the properties of water by passing weak salt brine (which can include sodium chloride or potassium chloride) through an electrolytic cell and temporarily changing the properties of the salt water into an oxidizing agent exhibiting antimicrobial properties. A sanitizer can include a 250-ppm hypochlorous acid (HOCl) solution. Another solution of catholyte, which is an alkaline cleaning/degreasing agent (which can also be made by sodium chloride or potassium chloride), can be produced as a byproduct of the electrolytic process. Still another solution can include negatively charged electrolyzed water.

To that end, the workflow 710 of FIG. 7 and the user interface screens 700A-M of FIGS. 7A-7M show operation of the filling station (100, 200) to dispense (including generate, create, or produce) various types of disinfectant, such as the disinfectant solution of 500-ppm hypochlorous acid (HOCl), a sanitizer of 250-ppm hypochlorous acid (HOCl), a cleaning/degreasing solution of sodium hydroxide, and an electrostatic solution. The dispensing can be done to different types of bottles or containers (151, 251), such as disinfectant bottles, sanitizer bottles, catholyte bottles, and electrostatic bottles, according to the techniques of the present disclosure. For simplicity, reference is made to the system 50 of FIGS. 2A-2B, but could equally apply with respect to the system 50 of FIG. 1.

Turning first to FIG. 7, the workflow 710 begins with the filling station 200 in a ready mode prepared to interact with a user and complete tasks (Block 712). When a user comes to the filling station 200, the use container (e.g., bottle) 251 is presented to the reader, scanner, or the like of the station (Block 714). The filling station 200 reads the container type, which can be stored on the tag 270 of the container 251, may be stored at the station 200, or may be remotely and associated with the ID of the read container 251 (Block 716). Based on the type of container 251, the filling station 200 prompts the user for an action (Block 718), and the station 200 receives the selection (Block 720). As disclosed herein, a number of user actions may be available for the user at the station 200. For the purposes of the present discussion, the selection is related to whether the presented container 251 is to be filled or not (Decision 722).

In filling procedures, the station 200 fills the container 251 with the solution pertaining to the type of container presented. Once filled, the container type, expiration date (e.g., filing date plus thirty days), and any other associated information is assigned to the tag 270 and stored at the tag 270 or in remote storage (Block 724). The user is then able to take the filled container 251 for use applications and to track use of the disinfectant, cleaning procedures, locations, and the like with a mobile application 267 of the disclosed system 50. The system 50 tracks the disinfectant's life cycle from that point based on the date and time information of the tracking devices (i.e., mobile device 265, filling station 200, etc.) and the assigned information of the subject container 251 (Block 726). Finally, in the process at the station 200, the user completes the desired tasks and is returned to the home screen (Block 728).

Figure 7A:
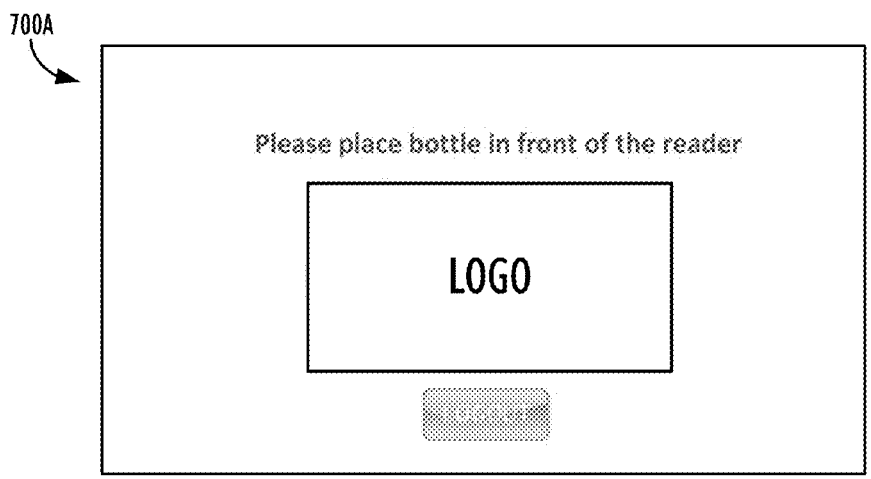

With an understanding of the workflow 710 of the present disclosure, discussion now turns to the example user interface screens 700A-M of FIGS. 7A-7M in interacting with a user. First, FIG. 7A shows an example user interface screen 700A of the filling station 200 being available for scanning/reading of any of the various types of use containers 251 or bottles in the system 50. Based on the reading of a tag 270 on a disinfectant bottle 251, for example, the filling station 200 presents an example user interface screen 700B as shown in FIG. 7B. The current expiration date of the contents of the bottle 251 can be read from storage or can be read as currently coded on the tag 270 of the use container 251 itself.

The screen 700B can include, but does not necessarily need to indicate a warning to the user that the disinfectant is expired because that warning can be provided through another mechanics, such as a mobile application 262 of a mobile device 260 as disclosed herein. Moreover, should the user try to use a use container 251 with expired disinfectant, protocols of the system 50 at the point-of-use can be provide warnings and prevent the disinfectant's use when the user operates the mobile application 262 of the mobile device 260, as disclosed herein. Additionally, the system 50 may not need to account for what amount of the disinfectant is poured out because the system 50 can instead let the user refill the use containers 251 every time. Accordingly, on the screen 700B, the user can seek to refill the use container 251 or not.

The user selecting to fill the use container 251 may result in a new expiration date being coded on the tag 270 of the use container 251 (and/or associating the date with stored information for the use container 251). Then, as shown in the screen 700C of FIG. 7C, the user can be instructed to empty the remaining contents of the use container 251 so it can be refilled with the new disinfectant. When finished, the coded information of the tag 270 can include the container's ID, new expiration date, user, etc. A completion screen 700D as shown in FIG. 7D can then follow, reiterating the new expiration date.

Figure 7E:
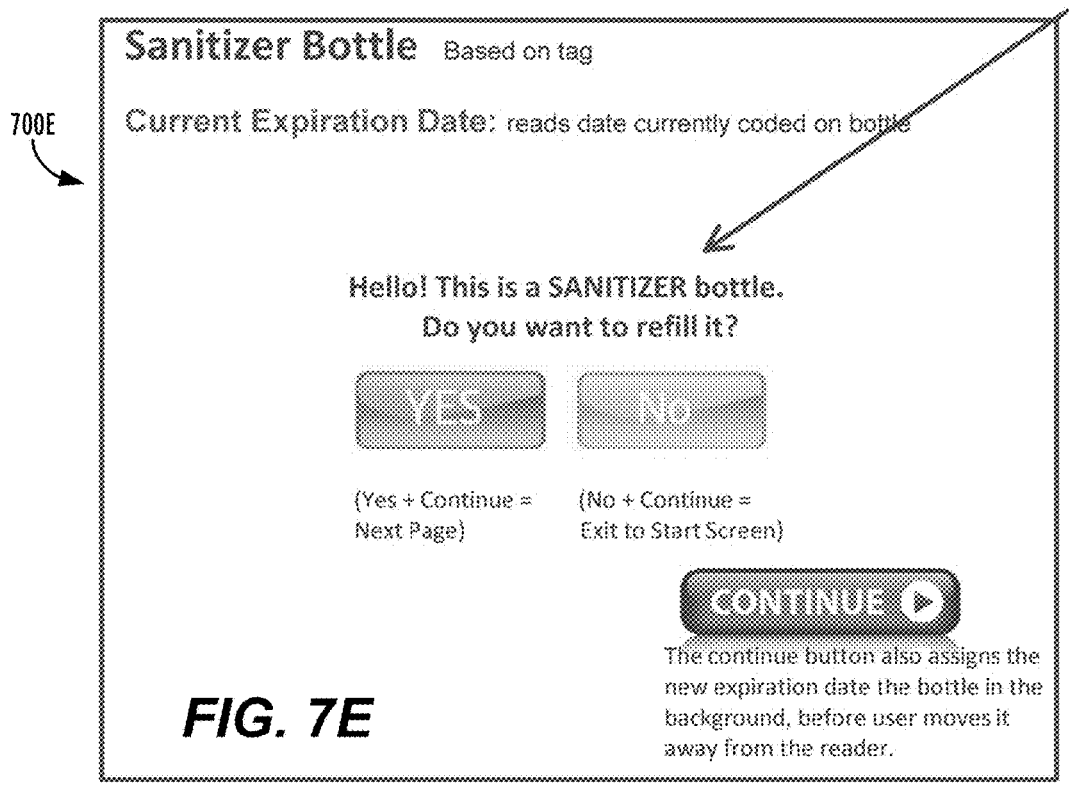
Figure 7F:
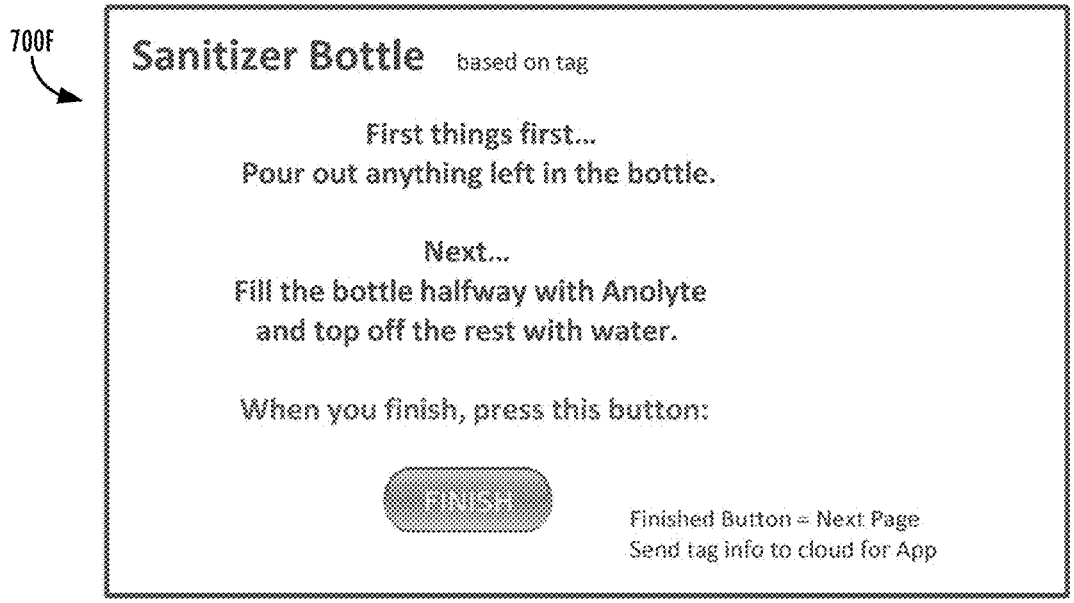

Based on the reading of a tag 270 on a sanitizer bottle 251, for example, the filling station 200 presents an example user interface screen 700E as shown in FIG. 7E. The current expiration date of the contents of the bottle 251 can be read from storage or can be read as currently coded on the tag 270 of the bottle 251. The user can then seek to refill the bottle 251 or not.

The user selecting to fill the bottle 251 may result in a new expiration date being coded on the tag 270 of the bottle 251 (and/or associating the date with stored information for the bottle 251). Then, as shown in the screen 700F of FIG. 7F, the user can be instructed to empty the remaining contents of the bottle 251, fill the bottle 251 half way with disinfectant, and then top off the rest with water so the bottle 251 can be refilled with the new sanitizer solution. When finished, the coded information of the tag 270 can include the bottle's ID, new expiration date, user, etc. A completion screen 700G as shown in FIG. 7G can then follow, reiterating the new expiration date.

Figure 7H:
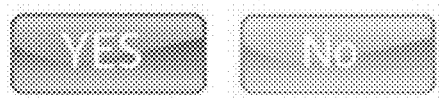
Figure 7I:

Based on the reading of a tag 270 on a catholyte bottle 251, for example, the filling station 200 presents an example user interface screen 700H as shown in FIG. 7H. The current expiration date of the contents of the bottle 251 can be read from storage or can be read as currently coded on the tag 270 of the bottle 251. The user can then seek to refill the bottle 251 or not.

Figure 7J:

The user selecting to fill the bottle 251 may result in a new expiration date being coded on the tag 270 of the bottle 251 (and/or associating the date with stored information for the bottle). Then, as shown in the screen 700I of FIG. 7I, the user can be instructed to empty the remaining contents of the bottle 251 and then fill the bottle 251 with the new solution. When finished, the coded information of the tag 270 can include the bottle's ID, new expiration date, user, etc. A completion screen 700J as shown in FIG. 7J can then follow, reiterating the new expiration date.

Based on the reading of a tag 270 on an electrostatic bottle 251, for example, the filling station 200 presents an example user interface screen 700K as shown in FIG. 7K. The current expiration date of the contents of the bottle 251 can be read from storage or can be read as currently coded on the tag 270 of the bottle 251. The user can then seek to refill the bottle 251 or not.

The user selecting to fill the bottle 251 may result in a new expiration date being coded on the tag 270 of the bottle 251 (and/or associating the date with stored information for the bottle). Then, as shown in the screen 700L of FIG. 7L, the user can be instructed to empty the remaining contents of the bottle 251 and then fill the bottle 251 with the new solution.

When finished, the coded information of the tag 270 can include the bottle's ID, new expiration date, user, etc. A completion screen 700M as shown in FIG. 7M can then follow, reiterating the new expiration date.

As noted above, the utilization of a particular use container 151 and 251 to perform a treatment in the facility can also be tracked by the system 50 using a mobile device 160, 260 such as a personal digital assistant, a tablet computer, a mobile telephone, or any other similar device and may be connected to the network 120, 220 (e.g., via a wireless network connection). In particular, each bottle/use container 151, 251 can be outfitted with a readable device 151L, 270, such as an NFC label, RFID tag, and/or a unique QR code, and each room/location of a facility can be outfitted with a readable device 180, 280, such as an NFC label, RFID tag, and/or a unique QR code. A mobile device 160, 260 having a mobile application 162, 262 can be used in conjunction with these devices 151L, 180, 270, 280 for tracking purposes disclosed herein.

An example of a readable device 750 is shown in FIG. 8A. As shown in FIG. 8B, a mobile software application 802 operating on a mobile device 800, such as a smart phone, utilizes an NFC device or other reader 804 of the mobile device 800 to read/scan a readable device 750 (e.g., a NFC decal, QR code, RFID tag, etc.) that is installed in every room and on the bottle(s)/container(s) used for cleaning.

Once the system 50 of the present disclosure assigns an expiration date to the disinfectant in the bottle(s)/container(s) (151, 251), the data is stored in cloud storage and/or within the data field of the RFID or NFC chip of the readable device 750. Before cleaning, a user taps or scans the readable device 750 of the bottle(s)/container(s) (151, 251) to be used for cleaning with the NFC device or other reader 804 of the mobile device 800 to ensure the disinfectant is still good or expired.

Figure 9A:
FIGS. 9A-9C show example mobile application screens indicating the status of the disinfectant in the subject bottle.
Figure 9B:
Figure 9C:

FIG. 9A shows an example screen 900A of the mobile application (802) indicating an alert that the disinfectant in the subject bottle (151, 251) is ready for use (i.e., has not expired). By contrast, FIG. 9B shows an example screen 900B of the mobile application (802) indicating an alert that the disinfectant in the subject bottle (151, 251) is not ready for use (i.e., has expired). Finally, FIG. 9C shows an example screen 900C of the mobile application (802) indicating an alert that the subject bottle (151, 251) needs to be filed. Thus, the system 50 can alert the expiration of the disinfectant associated with the tagged bottle (151, 251) to be used for the treatment of the location associated with a tagged label or device 750.

Figure 10A:
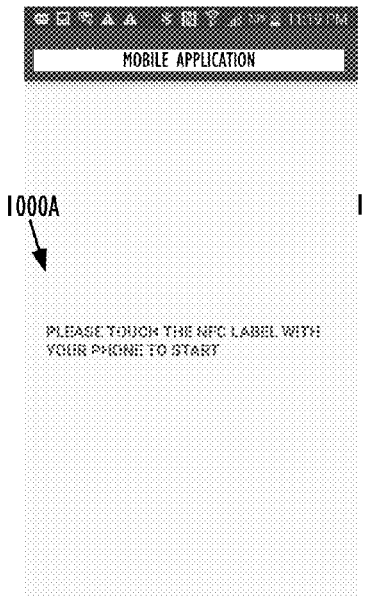
FIGS. 10A-10H show example mobile application screens having cleaning protocols provided to the user based on the room to be cleaned and other parameters.
Figure 10B:
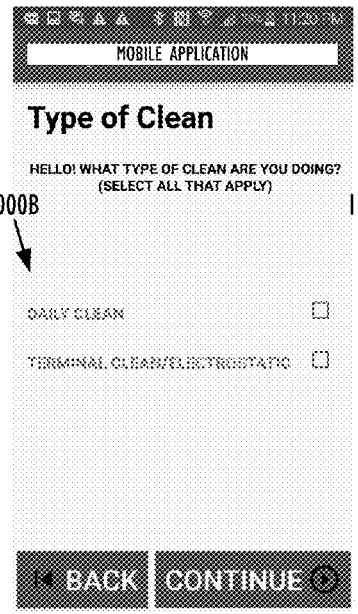

Once fresh disinfectant is ensured, the user continues the cleaning procedure that is established by the facility. Variable cleaning protocols can be stored in the system 50 and provided to the user on the mobile application (802) based on the room/location to be cleaned and other parameters. For example, the mobile application (802) as shown on the screen 1000A of FIG. 10A may instruct the user to use the mobile device (800) and touch the NFC label (750) or the like of the room/location to be cleaned. Based on the read NFC label (750), the mobile application (802) obtains the cleaning protocol(s) for that room/location from the system 50 and presents an instruction or selection screen 1000B on the mobile application (802), such as shown in FIG. 10B. Here, two example protocols are given—daily cleaning and terminal clean/electrostatic.

Protocols can, but do not necessarily have to be, variable or specific to the particular location/user. In other words, any number of protocols can be configured, stored, and presented for a particular implementation, and alerts can be provided to the user based on those protocols. For example, based on protocols, in addition to alerting to any expiration, the system 50 can alert that the disinfectant type associated with the tagged bottle (151, 251) is incorrect for use in the treatment of the location associated with tagged label.

Figure 10C:
Figures 10D, 10E, 10F:
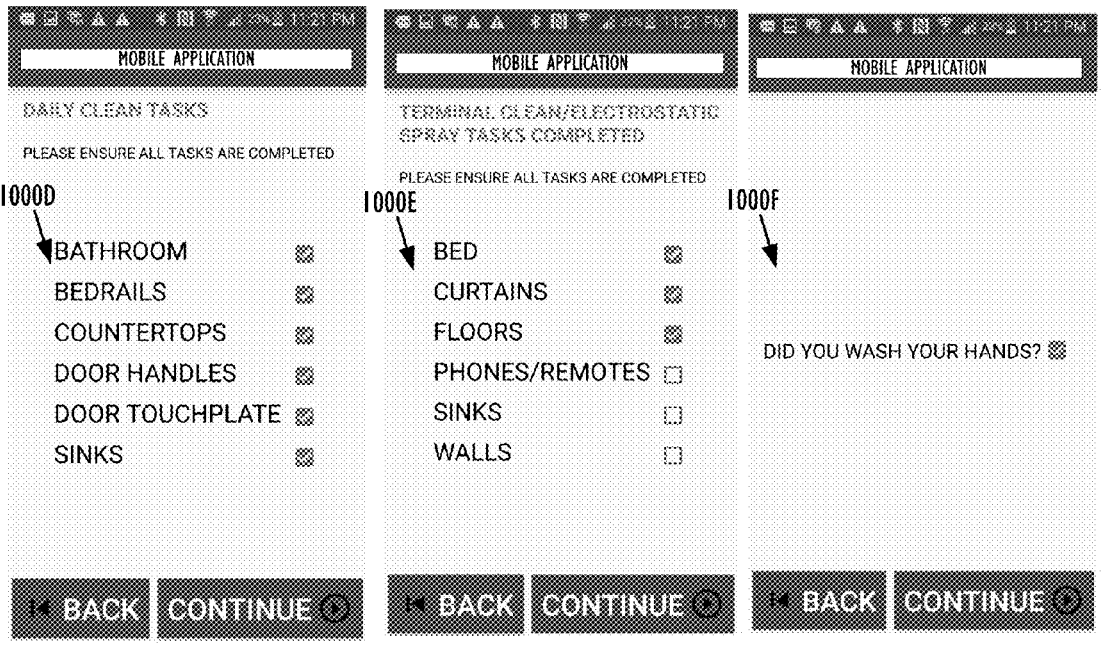
Figures 10G, 10H:
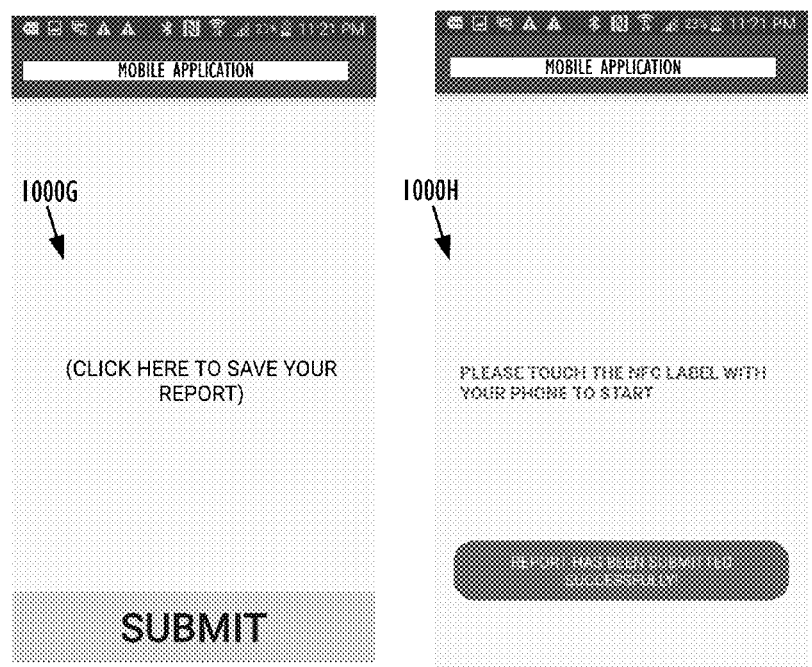

FIG. 10C shows an example screen 1000C of daily cleaning tasks for a room/location. Completion of the tasks can be tallied or checked, as shown in the screen 1000D of FIG. 10D. As another example, FIG. 10E shows an example screen 1000E of a terminal clean—i.e., a final cleaning of a room/location in which an electrostatic spray may be used. Upon completion of the tasks, the mobile device (800) may provide additional instructions or follow up, such as shown in the screen 1000F of FIG. 10F. Finally, the completion of the cleaning tasks can be saved for storage and reporting using the mobile application (802), as shown in the screen 1000G of FIG. 10G. The mobile application (802) as shown in the screen 1000H FIG. 10H is then ready for use in another room/location.

Once the data from the cleaning is submitted, the information is stored on the system (i.e., in cloud storage) so the information can be reviewed on other computers and devices. As noted herein, the stored information can include date, time, location, duration of cleaning, completed tasks, user, expiration date of disinfectant, etc. for the various tracking purposes disclosed herein.

FIG. 11 shows an example room report 1100 that may be generated based on stored information of a completed cleaning task. Such a report 1100 can be obtained remotely on the system based on stored information. Alternatively, the report can be accessed by utilizing the NFC device or other reader of the mobile device to read/scan a NFC decal, QR code, RFID tag, etc. for the room/location.

Use of the mobile application (802) by users on the mobile devices (800) allows for comprehensive reporting of valuable data for follow-up inspections and daily records of cleaning routines. Overall, the mobile application (802) ties the whole system 50 together by providing a complete process for producing and gathering data to ensure proper cleaning with unexpired disinfectant.

As will be appreciated, teachings of the present disclosure can be implemented in digital electronic circuitry, computer hardware, computer firmware, computer software, or any combination thereof. Teachings of the present disclosure can be implemented in a computer program product tangibly embodied in a machine-readable storage device for execution by a programmable processor so that the programmable processor executing program instructions can perform functions of the present disclosure. The teachings of the present disclosure can be implemented advantageously in one or more computer programs that are executable on a programmable system including at least one programmable processor coupled to receive data and instructions from, and to transmit data and instructions to, a data storage system, at least one input device, and at least one output device. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A system for monitoring treatment of locations of a facility with a disinfectant, the disinfectant being expirable and being dispensed from a plurality of portable containers, each portable container having a volume that is fillable repeatedly with the disinfectant for dispensing in the treatment, the system comprising:
   generation equipment configured to produce at least one type of the disinfectant;
   a plurality of first identifiers being electronically readable and being associated with the plurality of portable containers each having the volume that is fillable repeatedly with the at least one type of the disinfectant for dispensing in the treatment;
   communication equipment obtaining electronic input at least of each first identifier associated with the portable containers before dispensing in the treatment;
   at least one database associating first information of each first identifier for each portable container with each volume and each expiration of the at least one type of the disinfectant filled in and dispensed from each portable container;
   processing equipment operatively coupled to the at least one database and the communication equipment, the processing equipment tracking the first information using the electronic input and alerting an issue with the at least one type of the disinfectant in a given one of the portable containers before dispensing in the treatment based on the tracking; and
   a filling station having the generation equipment incorporated therein with at least one component of one or more of the communication equipment, the at least one database, and the processing equipment, the filling station configured as a point of generation and distribution to fill the portable containers with the at least one type of the disinfectant.

2. The system of claim 1, wherein the first identifiers comprise at least one of a Radio Frequency Identification tag, a bar code, a quick response (QR) code, a magnetic strip, a near field communication element, an optical element, and an electromagnetic element.

3. The system of claim 1, wherein the communication equipment comprises at least one reader electronically reading the first identifiers before dispensing in the treatment.

4. The system of claim 3, wherein the at least one reader is selected from the group consisting of a Radio Frequency Identification (RFID) reader, an optical scanner, a barcode reader, a Quick Response (QR) code reader, a magnetic strip reader, a near field communication device, an optical device, and an electromagnetic device.

5. The system of claim 1, wherein the processing equipment comprises one or more of a server, a computer, a tablet, a laptop computer, a kiosk, a cellular phone, and a smart phone.

6. The system of claim 1, wherein the communication equipment comprises a user interface associated with the processing equipment.

7. The system of claim 1, further comprising second identifiers being electronically readable and being associated with the locations for the treatment with the at least one type of the disinfectant, the at least one database associating the locations with the first information, the communication equipment obtaining the locations as part of the electronic input; the processing equipment further tracking the locations in conjunction with the first information.

8. The system of claim 7, wherein at least one of:
   to alert the issue, the processing equipment is configured to alert the expiration of the at least one type of the disinfectant associated with one of the first identifiers being used for the treatment of the location associated with one of the second identifiers;
   the communication equipment comprises at least one reader electronically reading the second identifiers; and
   to track the locations, the processing equipment is configured to associate a type of the treatment performed at the location, a user performing the treatment at the location, and a time of the treatment at the location.

9. The system of claim 7, wherein the at least one database associates second information of protocols for types of cleaning with the second identifiers for the locations; and wherein in the treatment of a given one of the locations with the at least one type of the disinfectant in a given one of the portable containers, the processing equipment is configured to obtain the protocol and the communication equipment is configured to provide the protocol to a user.

10. The system of claim 1, wherein to track the first information, the processing equipment is configured to at least one of:
   log the filling of each volume of the at least one type of the disinfectant in each portable container; and
   measure the at least one type of the disinfectant dispensed in the filling.

11. The system of claim 1, wherein to alert the issue with the at least one type of the disinfectant, the processing equipment is configured to execute one or more rules.

12. The system of claim 11, wherein the processing equipment in the one or more rules is configured to at least one of:
   generate an alert when the given portable container indicates containing the at least one type of the disinfectant past the expiration;
   automatically dispose of the at least one type of the disinfectant from the given portable container indicated to contain the disinfectant past the expiration; and
   instruct manual disposal of the at least one type of the disinfectant from the given portable container indicated to contain the at least one type of the disinfectant past the expiration.

13. The system of claim 1, wherein to track, the processing equipment is configured to determine that the given portable container contains the at least one type of the disinfectant past the expiration; and wherein to alert the issue, the processing equipment is configured to alert the expiration based on the determination.

14. The system of claim 1, wherein to track, the processing equipment is configured to determine that the volume of the at least one type of the disinfectant in the given portable container has been depleted; and wherein to alert the issue, the processing equipment is configured to alert the depletion based on the determination.

15. The system of claim 1, wherein one of the first identifiers identifies a distribution container being filled with the at least one type of the disinfectant at a source and transported to the facility for dispensing.

16. The system of claim 15, wherein another of the first identifiers identifies a use container of the portable containers, the use container being filled with the at least one type of the disinfectant from the distribution container for use at the facility.

17. The system of claim 1, wherein the first identifiers identify one or more use containers of the portable containers, the one or more use containers comprising at least one of a spray bottle, an electrostatic sprayer, a hand-sanitizer dispenser, a disinfectant container, and a sanitation container.

18. The system of claim 1, wherein the processing equipment comprises a local processing unit at the facility.

19. The system of claim 18, wherein the processing equipment further comprises a remote processing unit operatively coupled to the local processing unit via a network connection.

20. The system of claim 1, further comprising second identifiers being electronically readable and being associated with locations for the treatment with the at least one type of the disinfectant, the at least one database associating the locations with the first information; wherein the communication equipment comprises at least one device obtaining the first identifier for a given one of the portable containers and obtaining the second identifier for a given one of the locations; the processing equipment further tracking the treatment of the given location in conjunction with the first information of the given portable container.

21. The system of claim 20, wherein the at least one device comprises:
a first reader associated with the filling station and electronically reading the first identifier of the given portable container; and
a user interface having a second reader electronically reading the second identifier of the given location and being operable to associate the second identifier with the first identifier of the given portable container used.

22. The system of claim 21, wherein the second reader of the user interface electronically reads the first identifier to associate the first identifier with the second identifier.

23. The system of claim 1, wherein the generation equipment is configured to produce a plurality of the at least one type of the disinfectant.

24. The system of claim 23, wherein the types of the disinfectant produced by the generation equipment are selected from the group consisting of a first concentration of hypochlorous acid (HOCl) solution produced through an electrolytic process, a second concentration of hypochlorous acid (HOCl) solution produced through the electrolytic process and being less than the first concentration, a catholyte solution produced as a byproduct of the electrolytic process, a sodium hydroxide solution, a solution of negatively charged electrolyzed water, and an electrostatic solution.

25. The system of claim 1, wherein the at least one database associates each of the disinfectant types with the first information, and wherein the processing equipment tracks each of the disinfectant types in conjunction with the first information.

26. The system of claim 25, further comprising second identifiers being electronically readable and being associated with the locations for the treatment with the disinfectant types, the at least one database associating the locations with the first information, the communication equipment comprising at least one reader reading the first and second identifiers to obtain the electronic input including the locations; the processing equipment tracking the locations in conjunction with the first information.

27. The system of claim 26, wherein to alert the issue, the processing equipment is configured to alert the disinfectant type associated with one of the first identifiers being incorrect for use in the treatment of the location associated with one of the second identifiers.

28. A method of monitoring treatment of locations of a facility with a disinfectant, the disinfectant being expirable and being dispensed from a plurality of portable containers, each portable container having a volume that is fillable repeatedly with the disinfectant for dispensing in the treatment, the method comprising:
producing, with generation equipment, at least one type of the disinfectant;
filling, from a filling station, the portable containers with the at least one type of the disinfectant, the filling station configured as a point of generation and distribution and having the generation equipment incorporated therein with at least one component of one or more of communication equipment, at least one database, and processing equipment;
associating together, in the at least one database, first information of the plurality of portable containers each having the volume for the disinfectant that is fillable repeatedly with the at least one type of the disinfectant for dispensing in the treatment, the first information comprising each first identifier for each portable container with each volume and each expiration of the at least one type of the disinfectant filled in and dispensed from each portable container;
obtaining, with the communication equipment, electronic input at least of each first identifier associated with the portable containers before dispensing in the treatment;
tracking, with the processing equipment, the first information using the electronic input; and
alerting, with the processing equipment, an issue with the disinfectant in a given one of the portable containers before dispensing in the treatment based on the tracking.

29. The method of claim 28, wherein obtaining the electronic input comprises at least one of:
reading, with at least one reader of the communication equipment, the first identifier associated with the filling of the volume or with a check of the expiration of the volume before dispensing in the treatment; and
obtaining the electronic input from a user interface associated with the communication equipment.

30. The method of claim 28, wherein associating the first information in the at least one database further comprises associating second identifiers with the locations for the treatment with the at least one type of the disinfectant; wherein obtaining the electronic input with the communication equipment further comprises obtaining the second identifiers as part of the electronic input; and wherein tracking the first information with the processing equipment further comprises tracking the location in conjunction with the first information.

31. The method of claim 30, wherein tracking the locations comprises associating a type of the treatment performed, a user performing the treatment, and a time of the treatment.

32. The method of claim 30, further comprising associating, in the at least one database, second information of protocols for types of cleaning with the second identifiers for the locations; and wherein in the treatment of a given one of the locations with the at least one type of the disinfectant in a given one of the portable containers, the method comprises providing the protocol to a user with the communication equipment.

33. The method of claim 28, wherein alerting the issue comprises at least one of:
generating an alert when the given portable container indicates containing the at least one type of the disinfectant past the expiration;
automatically disposing of the at least one type of the disinfectant from the given portable container indicated to contain the at least one type of the disinfectant past the expiration; and
instructing manual disposal of the at least one type of the disinfectant from the given portable container indicated to contain the at least one type of the disinfectant past the expiration.

34. The method of claim 28, wherein producing the at least one type of the disinfectant with the generation equipment comprises producing a plurality of the at least one type of the disinfectant with the generation equipment.

35. The method of claim 34, wherein associating the first information in the at least one database further comprises associating each disinfectant type with the first information; and wherein tracking the first information with the processing equipment further comprises tracking each disinfectant type in conjunction with the first information.

36. The method of claim 35, wherein associating the first information in the at least one database further comprises associating second identifiers with the locations for the treatment with the more than one disinfectant type; wherein obtaining the electronic input with the communication equipment further comprises obtaining the second identifiers associated with the locations; and wherein tracking the first information with the processing equipment further comprises tracking the location in conjunction with the first information.

37. The method of claim 28, wherein tracking comprises at least one of:
determining that the given portable container contains the at least one type of the disinfectant past the expiration and alerting comprises alerting the expiration based on the determination; and
determining that the volume of the at least one type of the disinfectant in the given portable container has been depleted and alerting comprises alerting the depletion based on the determination.

38. A non-transitory program storage device having program instructions for controlling a programmable control device to perform a method of monitoring use of a disinfectant according to claim 28.

* * * * *